United States Patent
Kohyama

(10) Patent No.: US 8,771,196 B2
(45) Date of Patent: Jul. 8, 2014

(54) CUFF FOR BLOOD PRESSURE METER

(75) Inventor: Takuro Kohyama, Nishitokyo (JP)

(73) Assignee: Citizen Holdings Co., Ltd., Nishitokyo-shi (JP)

( * ) Notice: Subject to any disclaimer, the term of this patent is extended or adjusted under 35 U.S.C. 154(b) by 1442 days.

(21) Appl. No.: 12/225,315

(22) PCT Filed: Jan. 16, 2007

(86) PCT No.: PCT/JP2007/050449
§ 371 (c)(1),
(2), (4) Date: Sep. 18, 2008

(87) PCT Pub. No.: WO2007/111030
PCT Pub. Date: Oct. 4, 2007

(65) Prior Publication Data
US 2010/0234743 A1 Sep. 16, 2010

(30) Foreign Application Priority Data

Mar. 29, 2006 (JP) ................................. 2006-092286
Mar. 30, 2006 (JP) ................................. 2006-096100

(51) Int. Cl.
*A61B 5/02* (2006.01)
*A61B 3/12* (2006.01)
*A61B 5/022* (2006.01)

(52) U.S. Cl.
CPC .................................. *A61B 5/02233* (2013.01)
USPC ............ 600/485; 600/489; 600/497; 600/499

(58) Field of Classification Search
USPC .................... 600/499, 485, 489, 497
See application file for complete search history.

(56) References Cited

U.S. PATENT DOCUMENTS

| 4,605,010 | A | * | 8/1986 | McEwen | 600/499 |
| 5,188,115 | A | * | 2/1993 | Otani | 600/490 |
| 7,527,596 | B2 | * | 5/2009 | Ghigini | 600/499 |
| 2002/0099299 | A1 | * | 7/2002 | Inagaki | 600/499 |
| 2002/0112556 | A1 | * | 8/2002 | Rehle et al. | 74/443 |
| 2005/0288597 | A1 | | 12/2005 | Kishimoto et al. | |

FOREIGN PATENT DOCUMENTS

| EP | 1 013 220 | | 6/2000 |
| EP | 1013220 | * | 6/2000 |
| JP | H05-095920 | | 4/1993 |

* cited by examiner

*Primary Examiner* — Hong Sang
(74) *Attorney, Agent, or Firm* — Manabu Kanesaka

(57) ABSTRACT

It is an object to provide a cuff for blood pressure meter wherein a tightening mechanism and a holding mechanism have structures with good mechanical strength to enable the improvement of durability and a size reduction, fittability to an arm is improved to achieve higher accuracy of a blood pressure measurement, and operability can be improved.

A cuff for blood pressure meter (1) comprises a tightening mechanism (2) for tightening a flexible cuff (11), and a holding mechanism (3) for holding the tightening position of the tightened flexible cuff (11). The tightening mechanism (2) includes a rack (42) formed in a tightening belt (4), and a pinion gear (22). When the pinion gear (22) is rotated, the rack (42) is moved in a tightening direction. The holding mechanism (3) includes holding holes (43) formed at a plurality of positions in the longitudinal direction of the tightening belt (4), and holding pins (31) which engage into the holding holes (43). The holding pins (31) engage in the holding holes (43) so that the tightening position of the tightened flexible cuff (11) is held.

17 Claims, 18 Drawing Sheets

RELEASE DIRECTION

TIGHTENING DIRECTION (a)

(b)

(c)

CUFF FOR BLOOD PRESSURE METER

TECHNICAL FIELD

The present invention relates to a cuff for blood pressure meter. More particularly, this cuff for blood pressure meter provides good mechanical strength in a tightening mechanism and a holding mechanism. Thus, the cuff for blood pressure meter is improved in durability and reduced in size. The cuff for blood pressure meter is also improved in blood pressure measurement accuracy and operability. Moreover, the cuff for blood pressure meter comprises an elastic member which couples both ends of a flexible cuff together and which urges the flexible cuff in a release direction. This enables an arm to be easily inserted into and removed from the flexible cuff.

BACKGROUND ART

Recently, blood pressure meters have come into wide use in general households for the purpose of health care. A blood pressure meter for the general households typically comprises a measurement unit and a cuff for blood pressure meter. The measurement unit automatically measures and displays a blood pressure. The cuff for blood pressure meter has an air bag, etc. The measurement unit has enabled the blood pressure to be measured in a short time and with ease. However, it has been most troublesome for a user of the blood pressure meter to wind the cuff for blood pressure meter around the arm or remove the cuff for blood pressure meter from the arm.

Therefore, various techniques have been developed to improve such troublesome tasks and enable, for example, even an elderly person to easily make a measurement by himself.

PRIOR ART EXAMPLES

For example, a tightening device for blood pressure meter described in Patent document 1 has a curler, an actuator, a first rack, a double gear, a second rack and an electrode.

The curler tightens and fixes an air bag to an upper arm. The actuator is contracted in an electric field direction and expanded in a direction perpendicular to the electric field direction by the application of a voltage. The first rack is fixed to one end of the actuator. The double gear is disposed to gear with the first rack. The second rack is geared with the double gear. The electrode is disposed to apply the voltage.

The above-mentioned tightening device for blood pressure meter does not require complex mechanisms such as a motor and a clutch. Moreover, this tightening device for blood pressure meter is capable of tightening operation with higher response than the motor owing to a simplified configuration. Further, this tightening device for blood pressure meter is reduced in size and weight.

A blood pressure measurement cuff described in Patent document 2 comprises a case unit, a knob shaft and a cuff main body.

A rotating shaft, which is equipped with a feed roller and a driven gear, is provided inside the case unit. The knob shaft comprises a drive gear and an inner wheel. This drive gear is urged upward by a spring with respect to the case unit, and its lower end is screwed to the drive gear. Further, the upper end of the inner wheel is fitted into a knob cover via a spring ball. This inner wheel turns when the knob cover is turned. Moreover, a knob case spins free by a certain rotational load. The cuff main body has one end fixed to an appropriate part of the case unit, and the other end inserted in the case unit via the feed roller.

This blood pressure measurement cuff has an anti-reverse gear and a ratchet unit. The anti-reverse gear prevents the reversal of the knob shaft. The ratchet unit is geared with the anti-reverse gear. Thus, the diameter of the cuff main body decreases in the blood pressure measurement cuff when the knob cover is turned. When the knob cover is pressed down, the ratchet unit is removed, and the diameter of the cuff main body is restored to the original size in the blood pressure measurement cuff.

A cuff of blood pressure meter described in Patent document 3 has an air bag and an elastic plate therein. This elastic plate is provided outside the air bag, and holds the annular form of the elastic plate. Further, this elastic plate has a thin portion partly reduced in thickness in its arm axis direction. According to this cuff for blood pressure meter, the elastic plate (cuff) easily twists owing to the thin portion. Therefore, the cuff of blood pressure meter easily fits all shapes of arms including straight arms, tapered arms and the like.

Patent document 1: Japanese Patent Publication Laid-open No. 2006-6450

Patent document 2: Japanese Utility Model Publication Laid-open No. 2-37604

Patent document 3: Japanese Patent No. 3740985

DISCLOSURE OF THE INVENTION

Problem to be Solved by the Invention

On the other hand, in all of the above-mentioned blood pressure meters of the prior art examples, air is put into the air bag after the cuff is wound around the arm and tightened. At this moment, the arm is compressed, and great force acts to circumferentially press and expand the curler and the cuff main body.

However, in the tightening device for blood pressure meter described above, there is a risk that the teeth of the rack and the double gear may be broken off. In order to avoid this risk, it is necessary to carefully select the shapes, materials, etc. of the rack and the double gear, and it has been difficult to assure mechanical strength.

Moreover, although the above-mentioned blood pressure measurement cuff comprises the anti-reverse gear and the ratchet unit, there is a risk that the teeth of the anti-reverse gear may be broken off. In order to avoid this risk, it is necessary to carefully select the shape, material, etc. of the anti-reverse gear, and it has been difficult to assure mechanical strength.

The lack of the mechanical strength entails problems such as adverse effects on durability and fragility.

Furthermore, the tightening device for blood pressure meter can automatically open and close the curler, but has a problem of poor fittability in that the curler can not adapt to the shape of the arm. Another problem is that the scale of the structure is large and manufacturing costs can not be reduced.

Still further, in the above-mentioned blood pressure measurement cuff, when a spring with a high spring constant is used as a spring for urging the ratchet unit upward, great force is needed to rotate the knob cover. This also brings concern about decreased operability.

Further yet, in the above-mentioned tightening device for blood pressure meter and blood pressure measurement cuff, the cuff decreases its diameter while being held in a cylindrical shape. This makes it difficult to adapt to an arm in the shape of a truncated cone. Thus, in the case of, for example, a muscular arm, the arm is not uniformly compressed by the air bag, which is a problem in that the blood pressure can not be accurately measured in some cases.

Further yet, in the cuff of blood pressure meter described above, when the cuff is wound around the arm, one end of the elastic member is hooked to the arm for measurement so that the other end is wound around the arm. This work requires proficiency (knack). When a user winds the cuff by himself, the user has to hold the cuff with one hand to do the above-mentioned work requiring proficiency. The problem is that this work is hard for, for example, an elderly person with less finger mobility or a weaker grip.

Further yet, in the above-mentioned cuff of blood pressure meter, the thin portion partly reduced in thickness in its arm axis direction is formed in the elastic plate to improve fittability to various shapes of arms. However, in order to achieve this, the elastic plate generally has to be sufficiently flexible, but the elastic plate easily deforms if the elastic plate has a sufficiently flexible structure. That is, when the arm is inserted, it is necessary to maintain the expanded state of the elastic plate, and after the blood pressure measurement, it is necessary to open the elastic plate and then remove the arm, therefore, the easy deformation of the elastic plate leads to problem of degreased operability.

The present invention has been proposed to solve the above-mentioned problems with the conventional techniques. It is therefore an object of the present invention to provide a cuff for blood pressure meter wherein a tightening mechanism and a holding mechanism have structures with good mechanical strength to enable the improvement of durability and a size reduction, fittability to an arm is improved to achieve higher accuracy of a blood pressure measurement, and operability can be improved.

Means for Solving the Problem

In order to achieve the foregoing object, the present invention provides a cuff for blood pressure meter which tightens part of a living body by a tightening member, the cuff for blood pressure meter comprises: a tightening mechanism equipped with a rack and rack feed means for gearing with the rack; and a holding mechanism equipped with holding holes and holding members to be engaged into the holding holes, wherein the rack is formed integrally with the tightening member, and the holding holes are provided through the tightening member.

Thus, the rack is formed in the tightening member, so that it is possible to effectively use space and increase the size of the teeth of the rack and the rack feed means. Therefore, the mechanical strength of the tightening mechanism can be easily improved, and the tightening mechanism can be simplified and reduced in size. Moreover, the holding holes are formed in the tightening member and held by the holding members to be engaged therein, so that it is possible to effectively use space and improve the mechanical strength of the holding mechanism to achieve firm holding. Thus, the size of the holding mechanism can be reduced. Moreover, a holding strength can be calculated separately from the tightening mechanism, thereby enabling easy designing.

Furthermore, the tightening member is preferably belt-shaped.

This simplifies the structure and enables a reduction in size and weight.

Furthermore, the tightening member preferably includes a flexible cuff, and the rack is formed in the flexible cuff.

This reduces the number of components, and can reduce manufacturing costs. In addition, this flexible cuff generally has a portion having good flexibility to be wound around the arm in a fitting state, and a portion having good mechanical strength in which the rack is formed.

Furthermore, the tightening member preferably includes a flexible cuff, and a tightening belt wound around the outer periphery of the flexible cuff, and the rack is formed in the tightening belt.

This makes it possible to tighten the flexible cuff from its entire circumferential direction when the flexible cuff is tightened by the tightening mechanism. Therefore, a user can tighten the flexible cuff around the arm without discomfort. Moreover, when air is put into the air bag, force is dispersed over the entire circumferential direction of the tightening belt, so that it is possible to prevent sudden force from being applied to the holding mechanism, and improve the durability of the holding mechanism.

Furthermore, one end of the flexible cuff is preferably wound into the other end, and one end and the other end of the flexible cuff are coupled together by at least one of fabric, band and string elastic members which urges the flexible cuff in a release direction.

Thus, when the flexible cuff is untightened, the flexible cuff is automatically opened without fail by the resilience of the elastic member. Consequently, the arm can be easily and rapidly removed from the flexible cuff after the blood pressure measurement. Moreover, the flexible cuff is kept widely open by the resilience of the elastic member when the flexible cuff is untightened, so that the arm can be easily inserted into the flexible cuff.

Moreover, at least one of fabric, band and string elastic members is used as the elastic member. Thus, the elastic member flexibly deforms when the flexible cuff is tightened around the arm, so that it is possible to avoid the problem of an impaired fitted feeling. Moreover, since the flexibility of the cuff is not disturbed, it is possible to adapt to various shapes of arms. Therefore, even in the case of, for example, a muscular arm, the arm is uniformly compressed by the air bag, and the blood pressure can be accurately measured.

Furthermore, the fabric elastic member preferably has about the same width as the flexible cuff.

Thus, the flexible cuff and the elastic member become a substantially cylindrical annular member. This makes it possible to simplify the shape, improve the adaptability of the flexible cuff to the shape of the arm, and cause the tightening force of tightening means to also act on the upper and lower ends of the flexible cuff. Therefore, fittability can be further improved.

Furthermore, the tightening belt preferably holds a condition where one end of the flexible cuff is wound into the other end.

Thus, even when the air is put into the air bag, the tightening belt can hold the state of the flexible cuff. Moreover, when the flexible cuff is untightened, one end of the flexible cuff is kept wound into the other end. This makes it possible to improve the operability during the insertion of the arm into the flexible cuff.

Furthermore, the tightening belt preferably has a width equal to or more than 20% and equal to or less than 0.80% of the width of the flexible cuff, and is put in the center of the flexible cuff.

Thus, the part of the flexible cuff on which the tightening belt is not put deforms freely, and it is possible to adapt to an arm in the shape of a truncated cone. Consequently, the arm is uniformly compressed by the air bag, and the blood pressure can be accurately measured.

Furthermore, the rack is preferably provided on the longitudinal side surface of the tightening member, and the tooth thickness of the rack is equal to the thickness of the tightening member.

This makes it possible to simplify the structure, and reduce manufacturing costs.

Furthermore, the rack is preferably provided in an opening formed in the longitudinal direction of the tightening member.

This prevents the rack from projecting outward, so that the rack is less damaged, and the durability is improved.

Furthermore, the rack feed means is preferably a pinion gear, a worm gear or a worm.

This makes it possible to simplify the structure, and reduce manufacturing costs.

Furthermore, the holding members are preferably holding pins.

This makes it possible to achieve sufficiently high mechanical strength with a simple structure.

Furthermore, the tightening mechanism preferably has a knob to rotate the rack feed means, and the holding mechanism has urging means for urging the holding members in a direction to engage into the holding holes; when the knob is rotated in a tightening direction, the holding members come out of the holding holes against the urging force of the urging means; when the knob is further rotated in the tightening direction, the tightening member moves in the tightening direction; and when the holding holes located on the release direction side of the holding holes of which the holding members have come out move to the positions of the holding members, the holding members are engaged by the urging force into the holding holes which have been moved to.

Thus, the tightening member moves in the tightening direction as the holding members engage into the holding holes which have been moved to, so that the tightening member can tighten the part (upper arm) of the living body.

Furthermore, the knob preferably has a ratchet mechanism which rotates the rack feed means in the tightening direction, and a torque limiter mechanism.

Thus, owing to the torque limiter mechanism, it is possible to avoid a problem of excessive tightening by the user. It is also possible to ensure tightening up to a position preferable for a measurement. Moreover, owing to the ratchet mechanism, it is possible to avoid the problem of the breakage of the holding mechanism even if the user erroneously rotates the knob in a loosening direction.

Furthermore, the knob preferably includes noiseproof means.

This makes it possible to reduce noise produced when the ratchet mechanism and the torque limiter mechanism operate.

Furthermore, the noiseproof means is preferably a noise insulating member attached to the knob and/or a noiseproof sheet attached to a noise source in the knob.

This makes it possible to effectively reduce the noise. It is also possible to simplify the structure, and reduce manufacturing costs.

Furthermore, the holding mechanism preferably has a release lever to force the holding members out of the holding holes.

This ensures that the flexible cuff can be loosened by moving down the release lever, and operability can be improved.

Furthermore, the cuff for blood pressure meter preferably comprises an interference member which reduces impact noise produced when the release lever is closed.

This makes it possible to effectively reduce the impact noise. It is also possible to simplify the structure, and reduce manufacturing costs.

Furthermore, the tightening mechanism preferably has drive means for rotating the rack feed means.

This makes it possible to automate the tightening of the tightening member, and further improve usability.

Furthermore, the racks are preferably formed opposite to each other on both ends of the longitudinal direction of the tightening member.

This makes it possible to double a tightening distance corresponding to a rotation angle of the knob, and improve the mechanical strength of the tightening mechanism.

Furthermore, the rack is preferably a double rack.

This makes it possible to longitudinally move the tightening member in a balanced manner, and improve the mechanical strength of the tightening mechanism.

BEST MODE FOR CARRYING OUT THE INVENTION

First Embodiment

A first embodiment of a cuff for blood pressure meter of the present invention will hereinafter be described with reference to the drawings.

Figure 1:
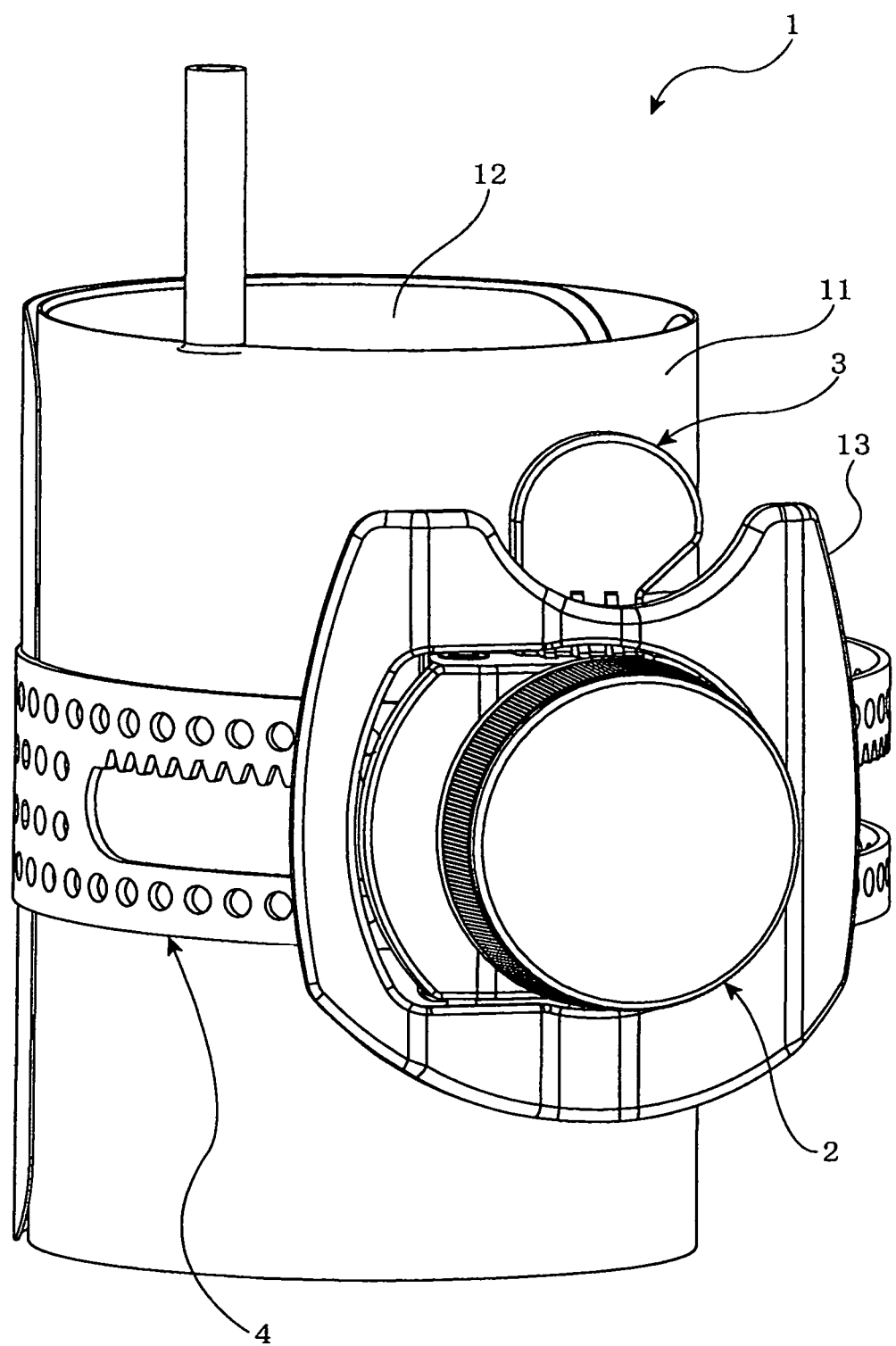
FIG. 1 shows a schematic perspective view of a first embodiment of a cuff for blood pressure meter of the present invention.

FIG. 1 shows a schematic perspective view of a first embodiment of a cuff for blood pressure meter of the present invention.

In FIG. 1, a cuff for blood pressure meter 1 comprises a tightening mechanism 2, a holding mechanism 3, a tightening belt 4 and a flexible cuff 11 as tightening members, an air bag 12 provided with a pipe 121, a protective cover 13, etc.

In this cuff for blood pressure meter 1, an arm (not shown) is inserted into the cylindrically rounded flexible cuff 11 when a blood pressure is measured. Then, when the flexible cuff 11 is wound up, the diameter of the flexible cuff 11 decreases. Thus, the flexible cuff 11 is wound around the arm.

<Flexible Cuff>

Figure 2:
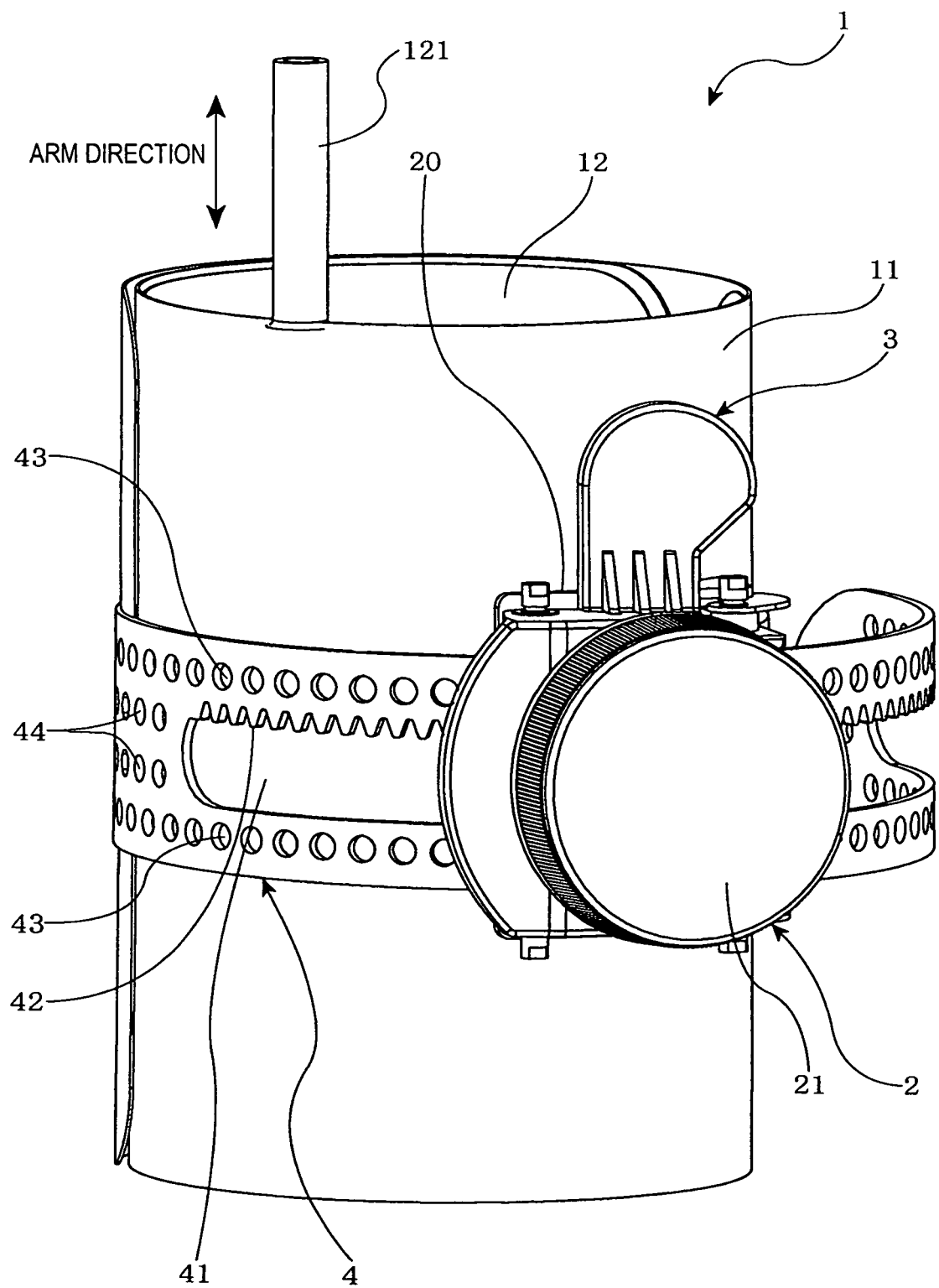
FIG. 2 shows a schematic perspective view in which a protective cover has been removed, according to the first embodiment of the cuff for blood pressure meter of the present invention.

FIG. 2 shows a schematic perspective view in which the protective cover has been removed, according to the first embodiment of the cuff for blood pressure meter of the present invention.

Figure 3:
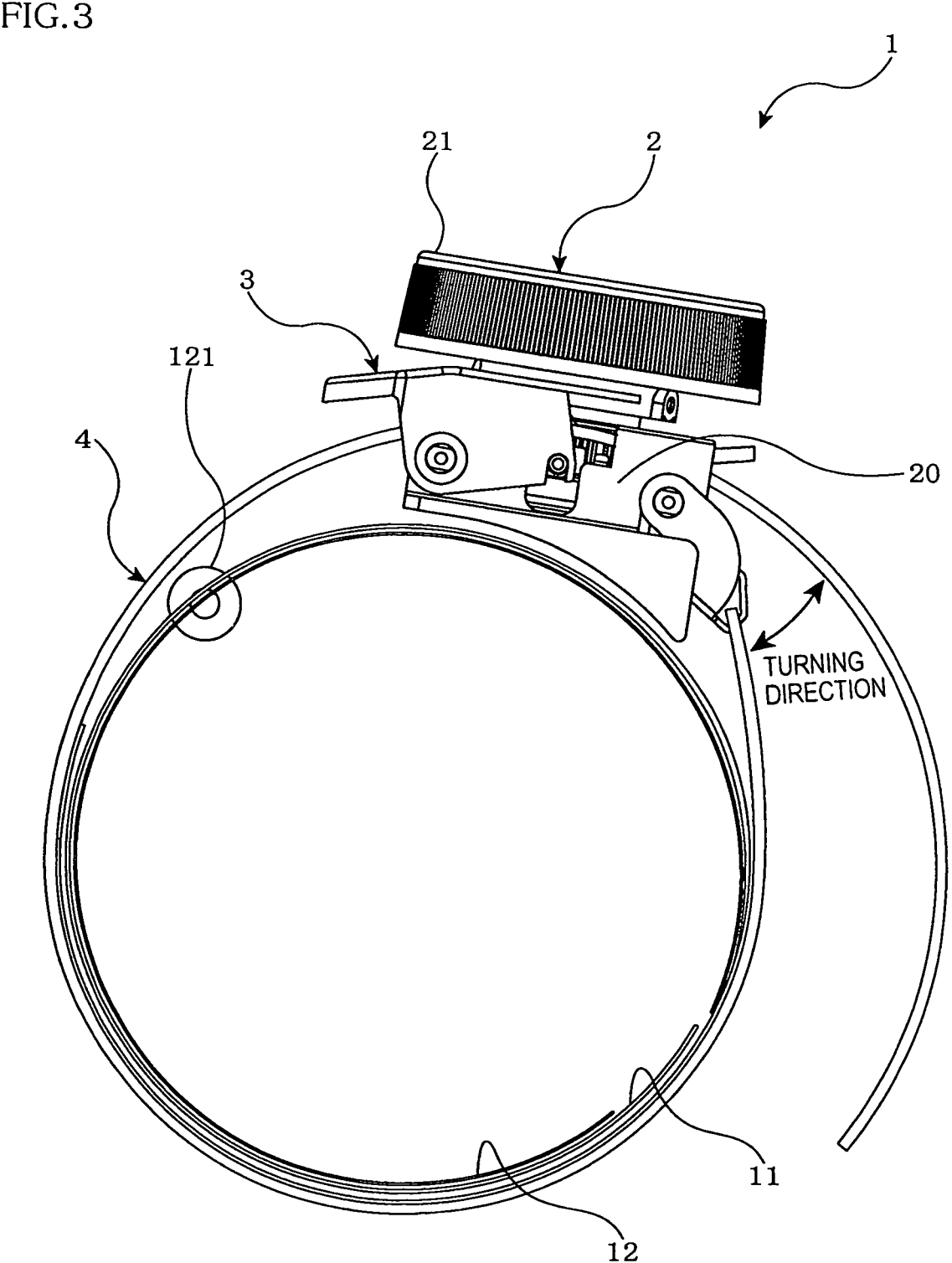
FIG. 3 shows a schematic bottom view of FIG. 2.

Furthermore, FIG. 3 shows a schematic bottom view of FIG. 2.

Figure 4:
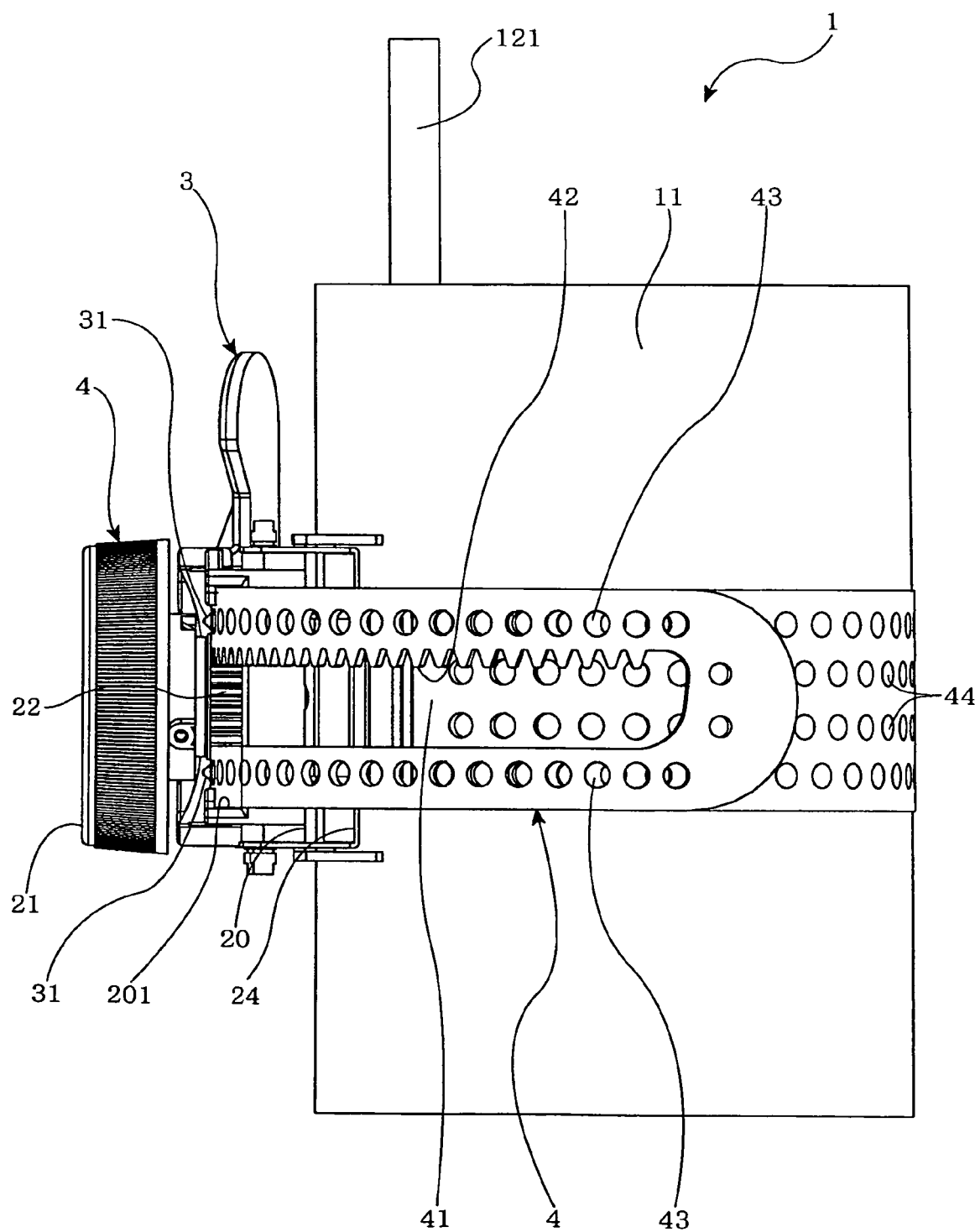
FIG. 4 shows a schematic side view of FIG. 2.

Moreover, FIG. 4 shows a schematic side view of FIG. 2.

In FIGS. 2, 3 and 4, the flexible cuff 11 (generally referred to as a cuff) is a resin cylindrical sheet. Both ends of the flexible cuff 11 in its longitudinal direction overlap each other about 180° in the circumferential direction. The flexible cuff 11 is flexible, and increases or decreases its diameter in accordance with the circumference of the arm.

Furthermore, the cylindrical air bag 12 is affixed to the inner surface of the flexible cuff 11. The pipe 121 is projectingly provided in the air bag 12 in the arm direction. Air is put into the air bag 12 via the pipe 121 when the blood pressure is measured.

<Tightening Belt>

The tightening belt 4 is a resin belt molded into an arc shape. A long-hole opening 41 is formed from substantially the center to the other end of the longitudinal direction of the tightening belt 4. A pinion gear 22 is housed in this opening 41. A rack 42 to be geared with the pinion gear 22 is formed in the upper part of the opening 41 (the side surface of the longitudinal direction of the opening 41). The thickness of the rack 42 is equal to the thickness of the tightening belt 4.

Furthermore, a plurality of holding holes 43 are provided side by side in the upper and lower parts of the width direction of the tightening belt 4 over the entire length. Holding pins 31 are engaged into the holding holes 43. The pitch of the holding holes 43 is smaller than double the diameter of the holding hole 43. This enables the fine adjustment of a holding position.

Moreover, in a part where the opening 41 is not formed, two through-holes 44 are disposed between the upper holding hole 43 and the lower holding hole 43. This permits the reduction of a material cost. Further, the rigidity of the part where the opening 41 is not formed is substantially equal to the rigidity of the part where the opening 41 is formed. Therefore, the flexible cuff 11 can maintain a substantially cylindrical shape regardless of the holding position.

In addition, the tightening belt 4 typically has a thickness of about 2 to 3 mm, and thus has sufficient mechanical strength for the rack 42.

One end of the longitudinal direction of the tightening belt 4 is coupled to a base 20 via a coupling plate 24. The coupling plate 24 is turnably supported by the base 20. Further, the other end of the longitudinal direction of the tightening belt 4 is charged into a groove 201 of the base 20. That is, the tightening belt 4 is wound around the outer periphery of the flexible cuff 11.

This makes it possible to tighten the flexible cuff 11 from its entire circumferential direction when the flexible cuff 11 is tightened by the tightening mechanism 2. Therefore, a user can tighten the flexible cuff around the arm without discomfort.

Moreover, when air is put into the air bag 12, force is dispersed over the entire circumferential direction of the tightening belt 4. Therefore, it is possible to prevent sudden force from being applied to the holding mechanism 3, and improve the durability of the holding mechanism 3.

Furthermore, the tightening belt 4 preferably has a width equal to or more than 20% and equal to or less than 80% of the width of the flexible cuff 11, and is put substantially in the center of the arm direction of the flexible cuff 11. Thus, the part of the flexible cuff 11 on which the tightening belt 4 is not put freely deforms, and it is possible to adapt to an arm in the shape of a truncated cone. Consequently, the arm is uniformly compressed by the air bag 12, and the blood pressure can be accurately measured. Here, the reason that the width of the tightening belt 4 is equal to or more than about 20% of the width of the flexible cuff 11 is as follows. If it is less than about 20%, the flexible cuff 11 can not be entirely tightened. Moreover, the reason that the width of the tightening belt 4 is equal to or less than about 80% of the width of the flexible cuff 11 is as follows. If it is more than about 80%, the part of the flexible cuff 11 that freely deforms is too small and it is impossible to adapt to various shapes of arms such as the truncated cone shape.

<Tightening Mechanism>

The tightening mechanism 2 comprises the rack 42 formed in the tightening belt 4, and the pinion gear 22. The pinion gear 22 is pressed into a rotating shaft 23 rotatably and projectingly provided in a bottom plate of the base 20. This pinion gear 22 is provided substantially in the center of the groove 201.

Furthermore, the tightening mechanism 2 has a knob 21 for rotating the pinion gear 22. The pinion gear 22 is screwed to this knob 21. The pinion gear 22 is pressed into the rotating shaft 23 while being screwed to the knob 21. Such a configuration makes it possible to effectively use space and increase the size of the teeth of the rack 42 and the pinion gear 22. Therefore, the mechanical strength of the tightening mechanism 2 can be easily improved, and the tightening mechanism 2 can be simplified and reduced in size.

In the tightening mechanism 2 of the present embodiment, the pinion gear 22 rotates clockwise when the user rotates the knob 21 clockwise. Thus, the rack 42 is moved in the tightening direction, and the tightening mechanism 2 tightens the flexible cuff 11.

Furthermore, lock portions 25 and projections 26 are respectively formed at four places of the groove 201. The lock portions 25 lock the surface of the tightening belt 4. The projections 26 are semispherical, and come in contact with the side surface of the tightening belt 4. This regulates the movement of the tightening belt 4 in a front surface direction and enables a smooth movement of the tightening belt 4. Moreover, the movement direction of the tightening belt 4 is adjusted so that the tightening belt 4 may not move obliquely.

Moreover, in the base 20, a contact plate 27 having a slope at the normal curvature radius of the flexible cuff 11 is projectingly provided in the direction of the flexible cuff 11 from the upper and lower end faces of the bottom plate. Thus, when the tightening belt 4 is tightened, the bottom surface of the base 20 does not directly contact the flexible cuff 11. Therefore, the cylindrical shape of the flexible cuff 11 is substantially maintained.

In addition, in the configuration of the present embodiment, the base 20 is not fixed to the flexible cuff 11 and is movable. However, the present invention is not limited to this configuration. For example, the base 20 may be fixed to the flexible cuff 11 by, for example, an adhesive.

<Holding Mechanism>

The holding mechanism 3 comprises the holding holes 43, a pair of holding pins 31, a spring 35 and a release lever 36.

The holding holes 43 are formed at a plurality of places in the longitudinal direction of the tightening belt 4 described above. The pair of holding pins 31 is engaged into the holding holes 43. The spring 35 as urging means urges the holding pins 31 in a direction to engage into the holding holes 43. The release lever 36 is used when the holding pins 31 are forced out of the holding holes 43.

The holding pins 31 are turnably supported by a shaft 32 at positions corresponding to the upper and lower holding holes 43. In addition, the shaft 32 is attached to the base 20 by bolts 34.

Furthermore, the spring (torsion spring) 35 is supported by a shaft 33. One end of the spring 35 urges the holding pins 31 in the direction to engage into the holding holes 43. In addition, the shaft 33 is attached to the base 20 by the bolts 34.

Moreover, the shaft 32, 33 is fixed to the base 20 by screwing the bolts 34 to its both ends. However, means for fixing the shaft 32, 33 is not limited to the bolts 34. For example, E-rings may be fitted into both ends of the shaft 32, 33 to fix the shaft 32, 33 to the base 20.

Figure 6:
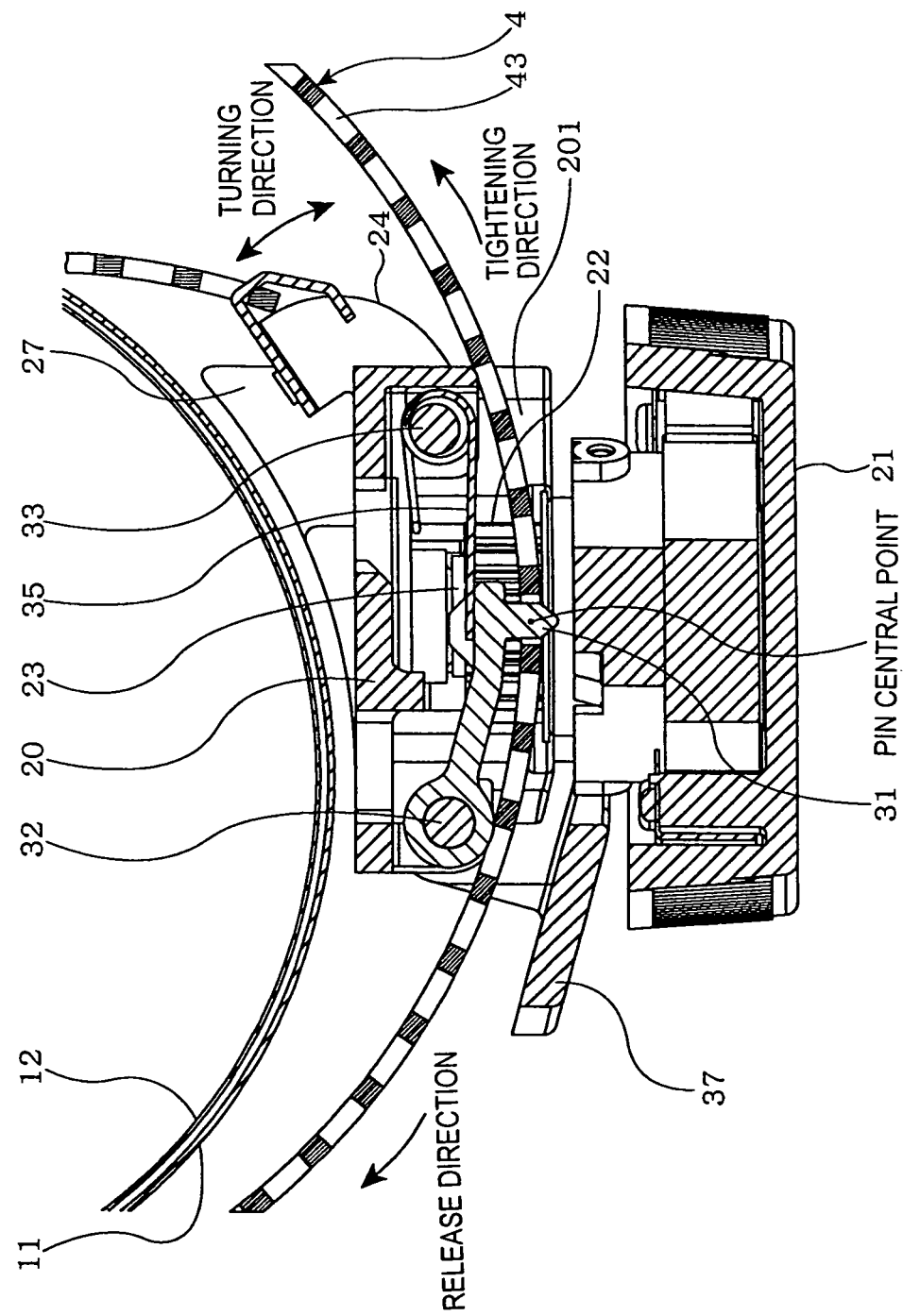
FIG. 6 shows a schematic enlarged sectional view in a top surface direction for explaining the tightening mechanism and the holding mechanism, according to the first embodiment of the cuff for blood pressure meter of the present invention.

Here, as shown in FIG. 6, the holding pin 31 is supported so as to turn around the shaft 32 provided on the diagonally upward left with respect to a pin central point. Thus, when the knob 21 is rotated clockwise (in the tightening direction), the sidewalls of the holding holes 43 in which the holding pins 31 have been engaged contact and press the holding pins 31. By the action of this force, the holding pins 31 which turn around the shaft 32 easily come out of the holding holes 43 against the urging force of the spring 35. Then, when the knob 21 is further rotated clockwise (in the tightening direction), the tightening belt 4 moves in the tightening direction. Then, when the holding holes 43 located on the release direction side of the holding holes 43 of which the holding pins have come out move to the positions of the holding pins 31, the holding pins 31 engage into the holding holes 43 which have been moved by the urging force of the spring 35. As the above-mentioned operation is repeated, the holding pins 31 are engaged into the holding holes 43 which have been moved to, one after another. Moreover, the tightening belt 4 moves in the tightening direction, and tightens the flexible cuff 11.

On the contrary, even if the tightening belt 4 attempts to move in the release direction while the holding pins 31 are engaged in the holding holes 43, the holding pins 31 do not come out of the holding holes 43 owing to the urging force of the spring 35 and the support position of the shaft 32. That is, since the holding pins 31 are kept engaged in the holding holes 43, the tightening position of the tightened flexible cuff 11 is held. Thus, the holding mechanism 3 effectively uses space, so that the holding mechanism 3 is easily improved in mechanical strength and achieves firm holding, and can be reduced in size. Moreover, a holding strength can be calculated separately from the tightening mechanism 2, thereby enabling easy designing.

Figure 5:
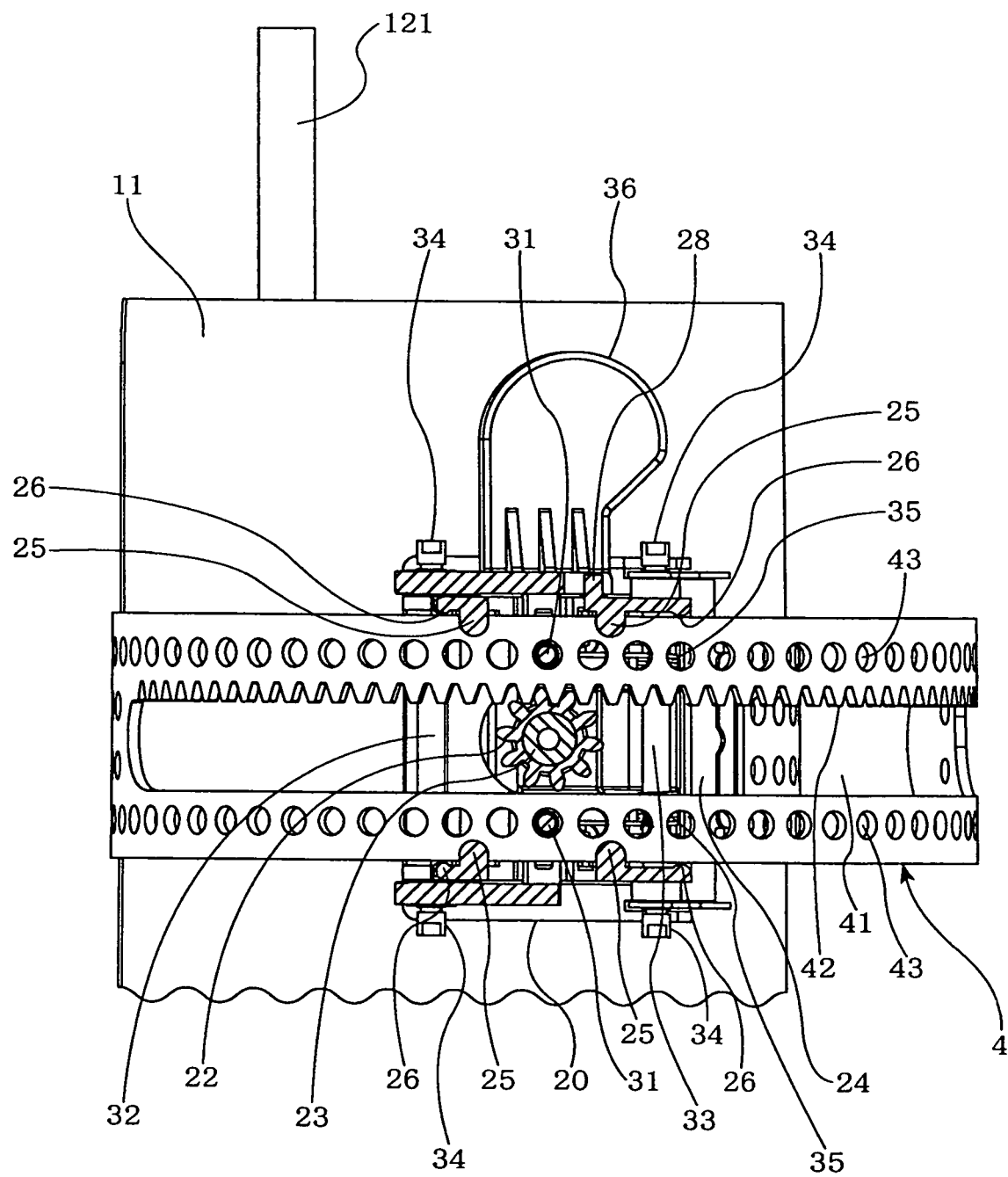
FIG. 5 shows a schematic sectional view in a front surface direction for explaining a tightening mechanism and a holding mechanism, according to the first embodiment of the cuff for blood pressure meter of the present invention.

Furthermore, in the holding mechanism 3, the release lever 36 is coupled to the holding pins 31 via a coupling portion 37. Thus, the release lever 36 and the coupling portion 37 are urged by the spring 35 in a direction (close direction) opposite to the flexible cuff 11. Further, the urged coupling portion 37 contacts a stopper 28 (see FIG. 5) of the base 20. Thus, the pin central point of the holding pins 31 is located substantially in the center of the thickness direction of the tightening belt 4 (see FIG. 6).

Figure 7:
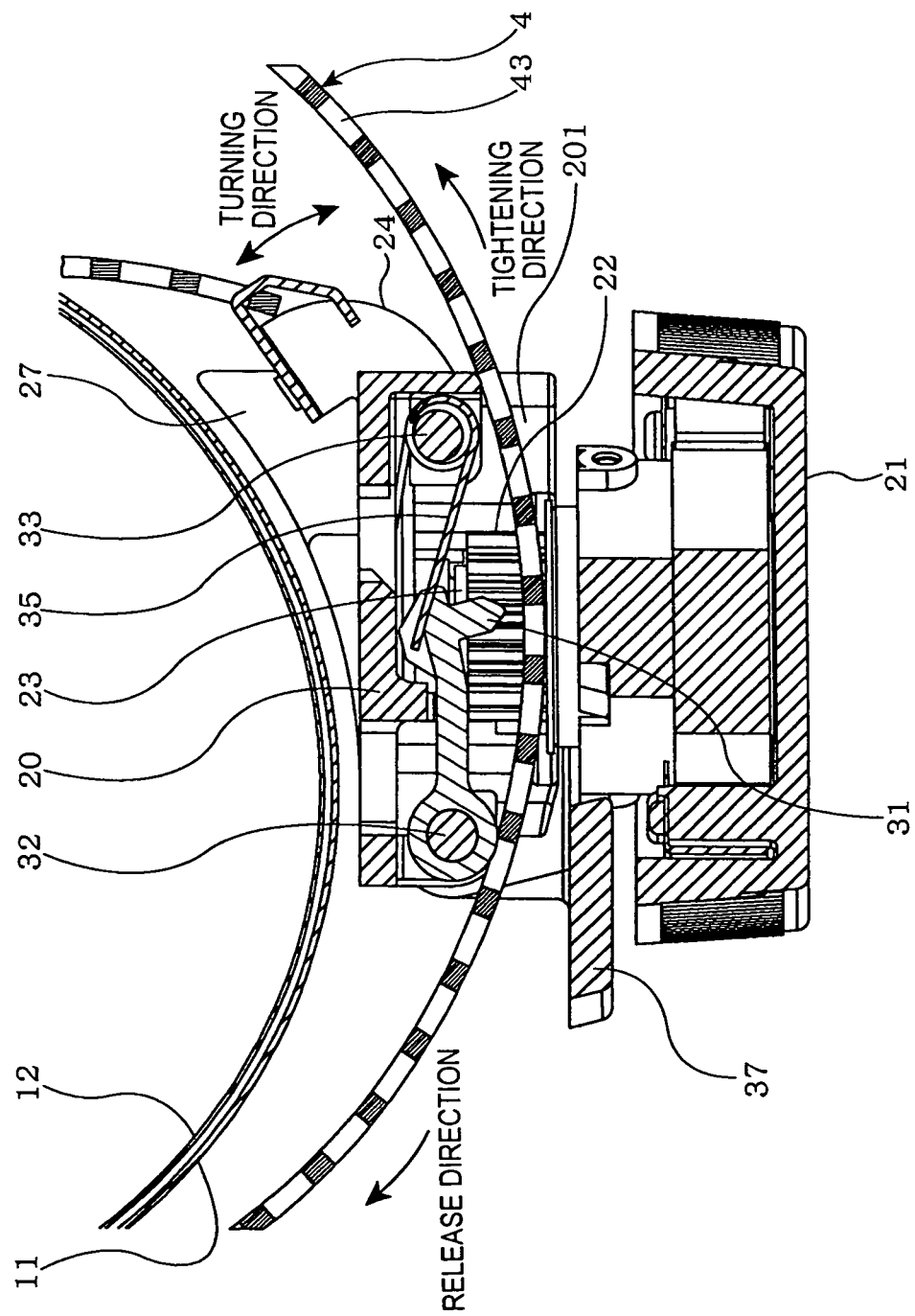
FIG. 7 shows a schematic enlarged sectional view in the top surface direction for explaining a condition where a release lever is moved down, according to the first embodiment of the cuff for blood pressure meter of the present invention.

When the flexible cuff 11 is untightened, the release lever 36 is pushed in a direction (open direction) to the flexible cuff 11. Owing to this operation, the coupling portion 37 and the holding pins 31 turn counterclockwise, and the holding pins 31 come out of the holding holes 43, as shown in FIG. 7. Then, the tightening belt 4 moves in the release direction, and the flexible cuff 11 is untightened. That is, the flexible cuff 11 can be easily loosened without fail by moving down the release lever 36, and operability is improved.

<Knob>

Figure 8:
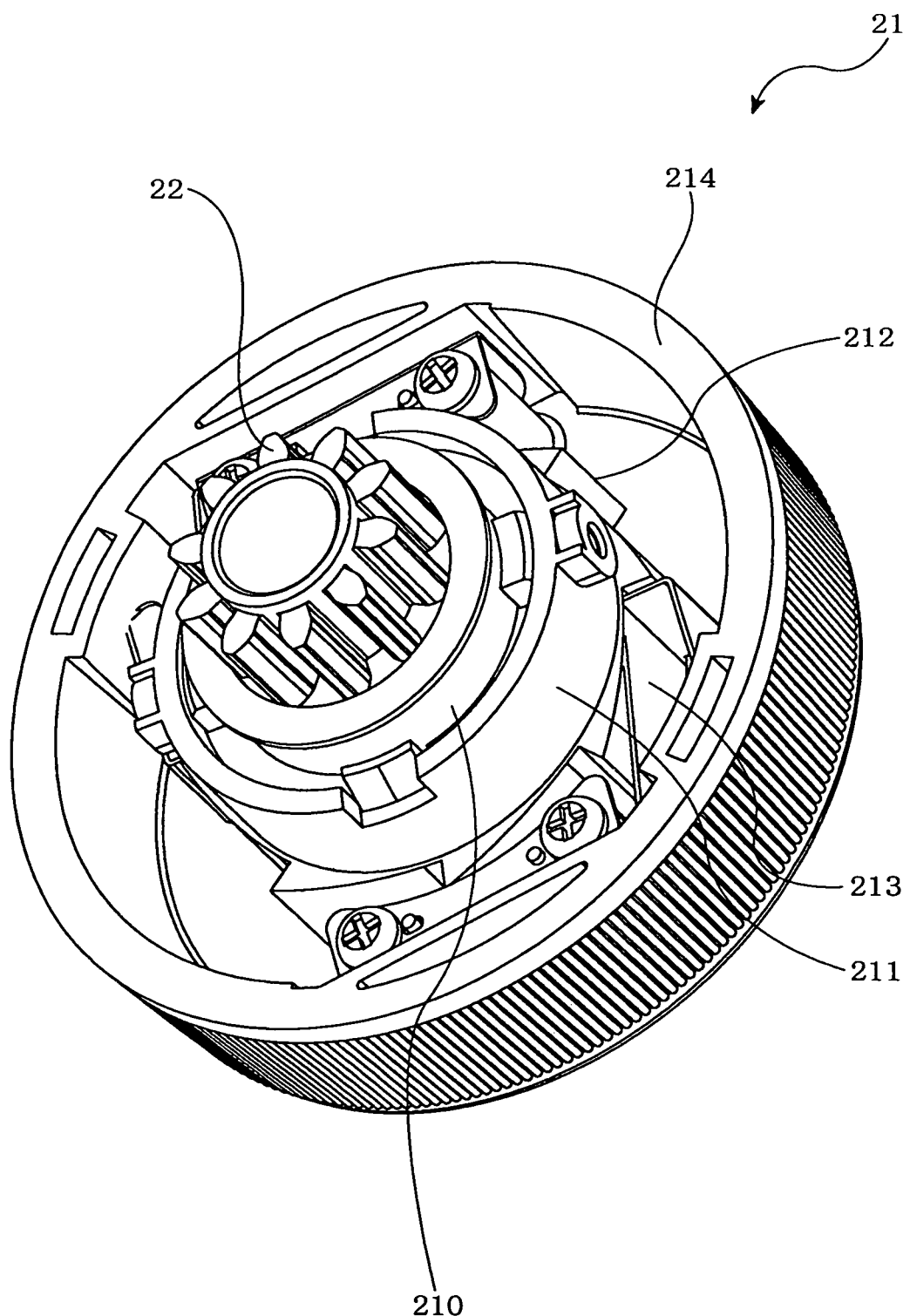
FIG. 8 shows a schematic enlarged perspective view for explaining the structure of a knob, according to the first embodiment of the cuff for blood pressure meter of the present invention.

FIG. 8 shows a schematic enlarged perspective view for explaining the structure of the knob, according to the first embodiment of the cuff for blood pressure meter of the present invention.

Figure 9:
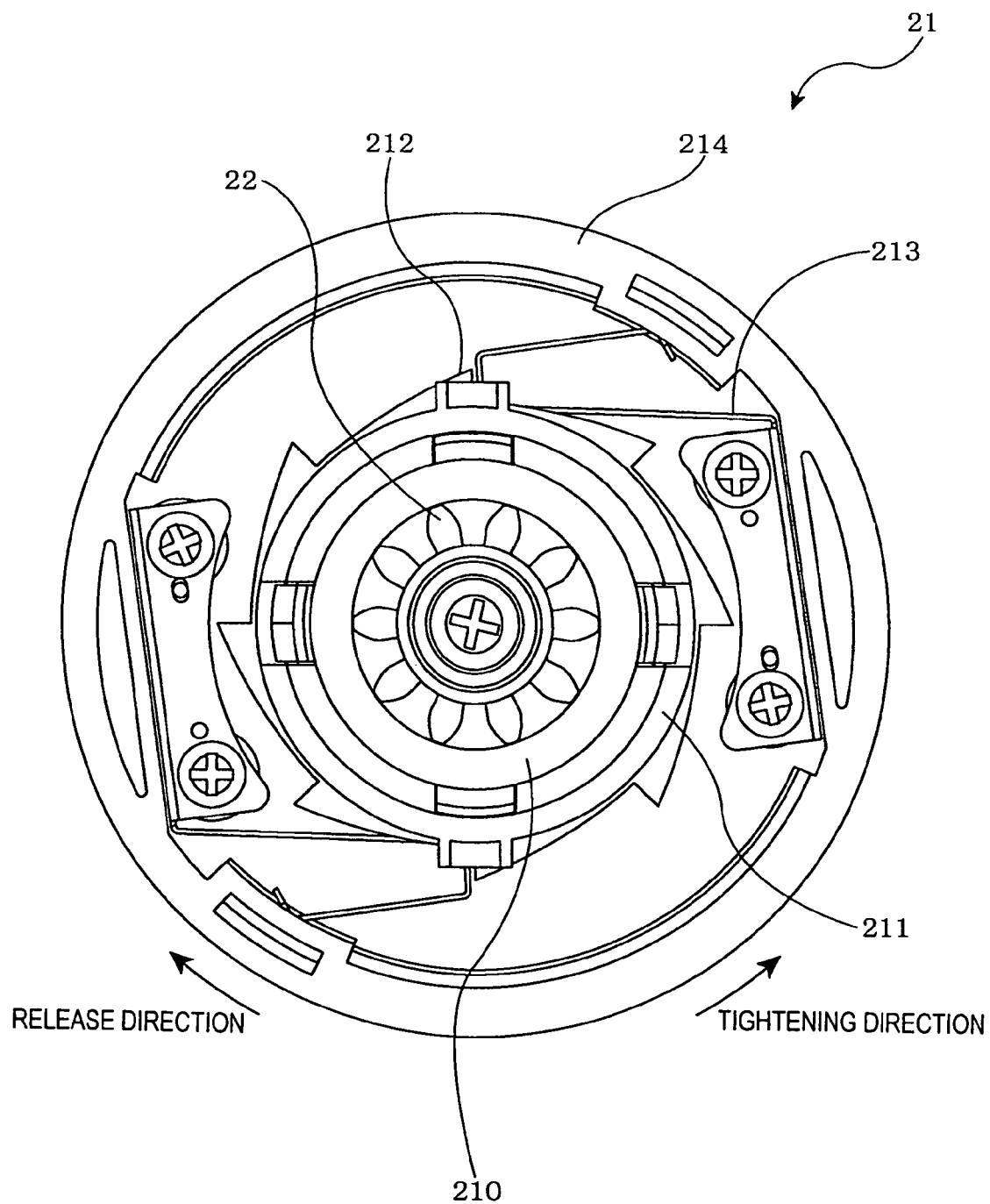
FIG. 9 shows a schematic enlarged plan view for explaining the structure of the knob, according to the first embodiment of the cuff for blood pressure meter of the present invention.

Furthermore, FIG. 9 shows a schematic enlarged plan view for explaining the structure of the knob, according to the first embodiment of the cuff for blood pressure meter of the present invention.

In FIGS. 8 and 9, the knob 21 comprises a knob main body 210, the pinion gear 22, a ratchet wheel 211, a wheel 214 and a pair of leaf springs 213.

The knob main body 210 is in a bottomed cylindrical shape. The pinion gear 22 is screwed into the knob main body 210 in a partially fitted state. The ratchet wheel 211 is projectingly provided with eight ratchets 212, and is screwed to the outer peripheral side surface of the knob main body 210. The wheel 214 is in a bottomed cylindrical shape, and is rotatably provided at the bottom (on the opposite side of the pinion gear 22) of the knob main body 210. The pair of leaf springs 213 is formed into a substantially U-shape, and is provided symmetrically with respect to the center of the knob 21.

One end of the leaf spring 213 is screwed to the wheel 214, and the other end thereof movably comes in contact with the inner side surface of the wheel 214. Further, the contact surface of the leaf spring 213 on the side of the ratchet wheel 211 is substantially opposite to the ratchet 212. This leaf spring 213 functions as a detent in a ratchet mechanism. This ratchet mechanism has a torque limiter function.

When the user rotates the wheel 214 in the release direction, the leaf spring 213 climbs over the slope of the ratchet 212, so that the pinion gear 22 does not rotate in the release direction and is kept stopped. On the contrary, when the wheel 214 is rotated in the tightening direction by torque smaller than set tightening torque, the contact surface of the leaf spring 213 presses the ratchet 212, so that the ratchet wheel 211, the knob main body 210 and the pinion gear 22 rotate in the tightening direction. When the wheel 214 is rotated in the tightening direction by torque equal to or more than the set tightening torque, the contact surface of the leaf spring 213 contacts the ratchet 212, but the leaf spring 213 deforms and climbs over the ratchet 212, so that the pinion gear 22 does not rotate in the tightening direction and is kept stopped.

As described above, the knob 21 of the present embodiment has the ratchet mechanism which rotates the pinion gear 22 in the tightening direction, and a torque limiter mechanism. Owing to the torque limiter mechanism, the knob 21 avoids a problem of excessive tightening by the user, and ensures tightening up to a position preferable for a measurement. Moreover, owing to the ratchet mechanism, the problem of the breakage of the holding mechanism is avoided even if the user erroneously rotates the knob 21 in the loosening direction with strong force.

In addition, the pinion gear 22 is provided in the knob 21 in the present embodiment. However, the present invention is not limited to this. For example, the pinion gear 22 may be provided in the base 20, and the knob 21 may rotate the pinion gear 22 via, for example, a joint.

The use and operation of the cuff for blood pressure meter 1 having the above-mentioned configuration are described.

First, the user of the cuff for blood pressure meter 1 who is to have the blood pressure measured presses down the release lever 36 in the direction of the flexible cuff 11. Thus, in the cuff for blood pressure meter 1, the tightening belt 4 moves in the release direction by the resilience of the tightening belt 4 and/or the flexible cuff 11, and the diameters of the flexible cuff 11 and the air bag 12 increase.

Subsequently, the user lays the cuff for blood pressure meter 1 on its side so that the knob 21 is directed upward, and inserts, for example, the left arm into the air bag 12.

Then, the user rotates the knob 21 clockwise (in the tightening direction). Owing to this operation, the pinion gear 22 sends the rack 42 in the tightening direction, and the tightening belt 4 moves in the tightening direction, and moreover, the diameters of the flexible cuff 11 and the air bag decrease. In the meantime, the holding pins 31 are repeatedly engaged in and out of the holding holes 43 in the holding mechanism 3. At this point, when there is a gap between the left arm and the air bag 12, the knob 21 can be rotated by small force.

Then, when the user further rotates the knob 21 clockwise (in the tightening direction), the diameters of the flexible cuff 11 and the air bag 12 further decrease, and no gap remains between the left arm and the air bag 12, and moreover, the torque to rotate the knob 21 increases. Therefore, the user rotates the knob 21 with force corresponding to this torque. The user rotates the knob 21 with greater force in accordance with the gradually increasing torque. When set torque is reached, the torque limiter mechanism of the knob 21 is actuated, and the wheel 214 of the knob 21 spins free. At this point, the holding pins 31 have already been engaged in the holding holes 43, so that the tightened state of the flexible cuff 11 is satisfactorily maintained.

Then, air is put into the air bag 12, and the blood pressure is measured.

At this point, great force acts on the tightening belt 4 in the circumferential direction when the air is put into the air bag 12. As described above, in the cuff for blood pressure meter 1, the holding pins 31 are engaged in the holding holes 43 of the tightening belt 4, so that the tightening position of the flexible cuff 11 can be held.

Then, the measurement of the blood pressure is displayed, and when the air is removed from the air bag 12, the user presses down the release lever 36. Thus, in the cuff for blood pressure meter 1, the tightening belt 4 moves in the release direction by the resilience of the tightening belt 4 and/or the flexible cuff 11, and the diameters of the flexible cuff 11 and the air bag 12 increase.

Then, the user removes the left arm from the air bag 12, returns the cuff for blood pressure meter 1, and finishes the blood pressure measurement.

As described above, according to the cuff for blood pressure meter 1 of the present embodiment, the tightening mechanism 2 and the holding mechanism 3 have the structures with good mechanical strength, thereby enabling an improvement in durability and a size reduction. Moreover, the flexible cuff 11 can be adapted to the shape of the arm, so that an erroneous measurement can be prevented, and the accuracy of a blood pressure measurement can be improved. Still further, the knob 21 and the release lever 36 can be securely operated with one hand, so that it is possible to eliminate the traditional feeling that the tightening of the cuff for blood pressure meter 1 is troublesome.

Moreover, in the configuration of the embodiment described above, the opening 41 is formed on the other end of the tightening belt 4, and the rack 42 is formed on one side (upper side) of the opening 41, but the present invention is not limited to this.

Figure 10:
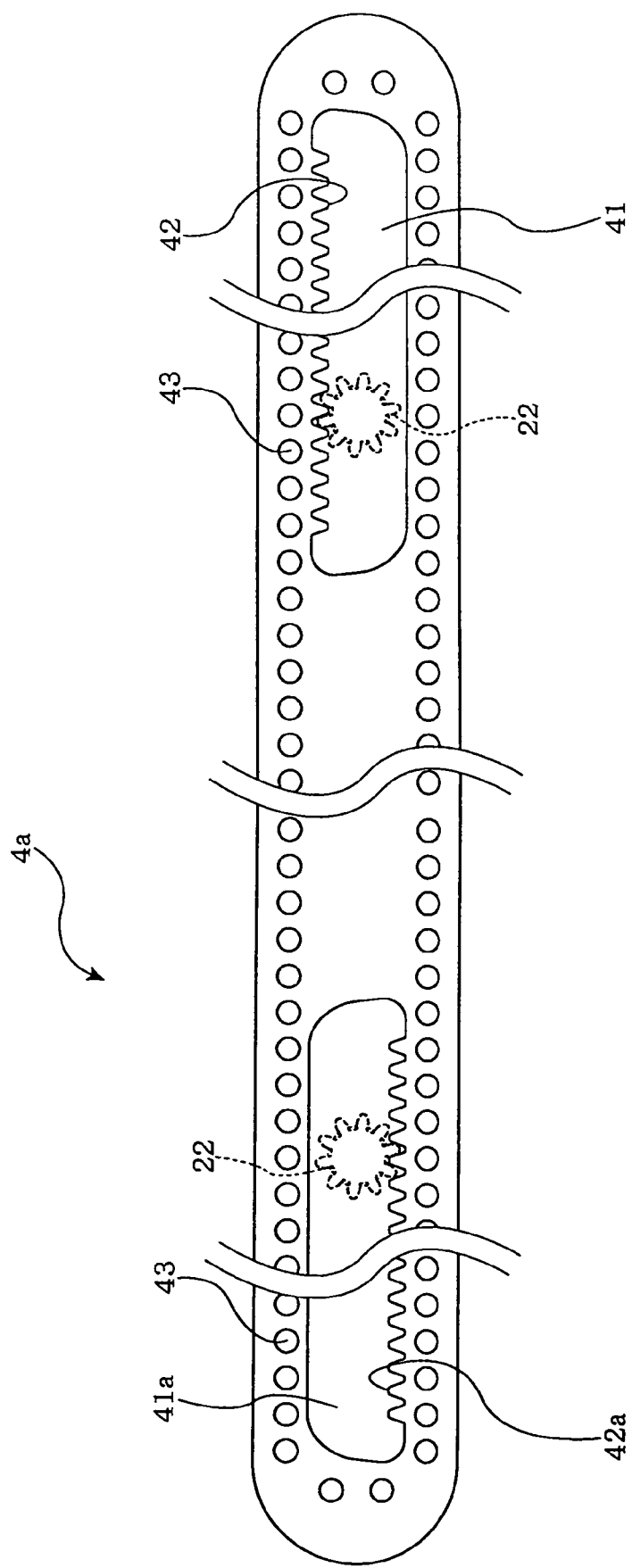
FIG. 10 shows a schematic enlarged plan view for explaining a tightening belt, according to a first application of the first embodiment of the cuff for blood pressure meter of the present invention.

For example, as shown in FIG. 10, a tightening belt 4a may be used in which an opening 41a is formed on one end in the longitudinal direction so that a rack 42a is formed on the lower side of the opening 41a, and the opening 41 is formed on the other end so that the rack 42 is formed on the upper side of the opening 41. This makes it possible to double a tightening distance corresponding to a rotation angle of the pinion gear 22, and improve the mechanical strength of the tightening mechanism 2.

Figure 11:
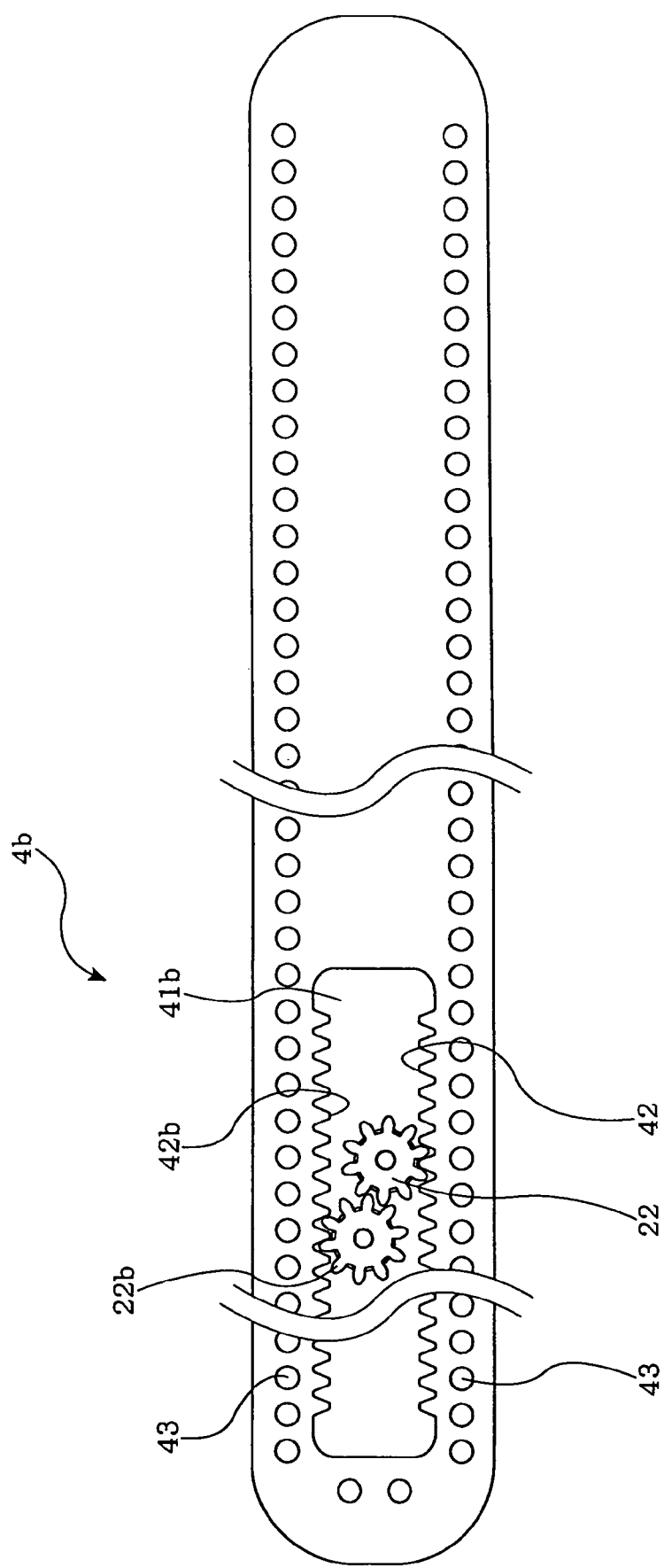
FIG. 11 shows a schematic enlarged plan view for explaining a tightening belt, according to a second application of the first embodiment of the cuff for blood pressure meter of the present invention.

Moreover, as shown in FIG. 11, a tightening belt 4b may be used in which an opening 41b is formed on one end of the longitudinal direction, so that the rack 42 is formed on the lower side of the opening 41b, and a rack 42b is formed on the upper side of the opening 41b. Then, the tightening belt 4b is screwed to the pinion gear 22, and a pinion gear 22b which is screwed to the rack 42b is provided, so that a double rack structure is provided. This makes it possible to longitudinally move the tightening belt 4b in a balanced manner, and improve the mechanical strength of the tightening mechanism.

Second Embodiment

A second embodiment of a cuff for blood pressure meter of the present invention will hereinafter be described with reference to the drawings.

The cuff for blood pressure meter of the present embodiment is different from the cuff for blood pressure meter 1 in the first embodiment in that it comprises a flexible cuff 11c having a fabric elastic member instead of the flexible cuff 11. It is to be noted that the configuration is substantially similar to that in the first embodiment in other respects.

Figure 12:
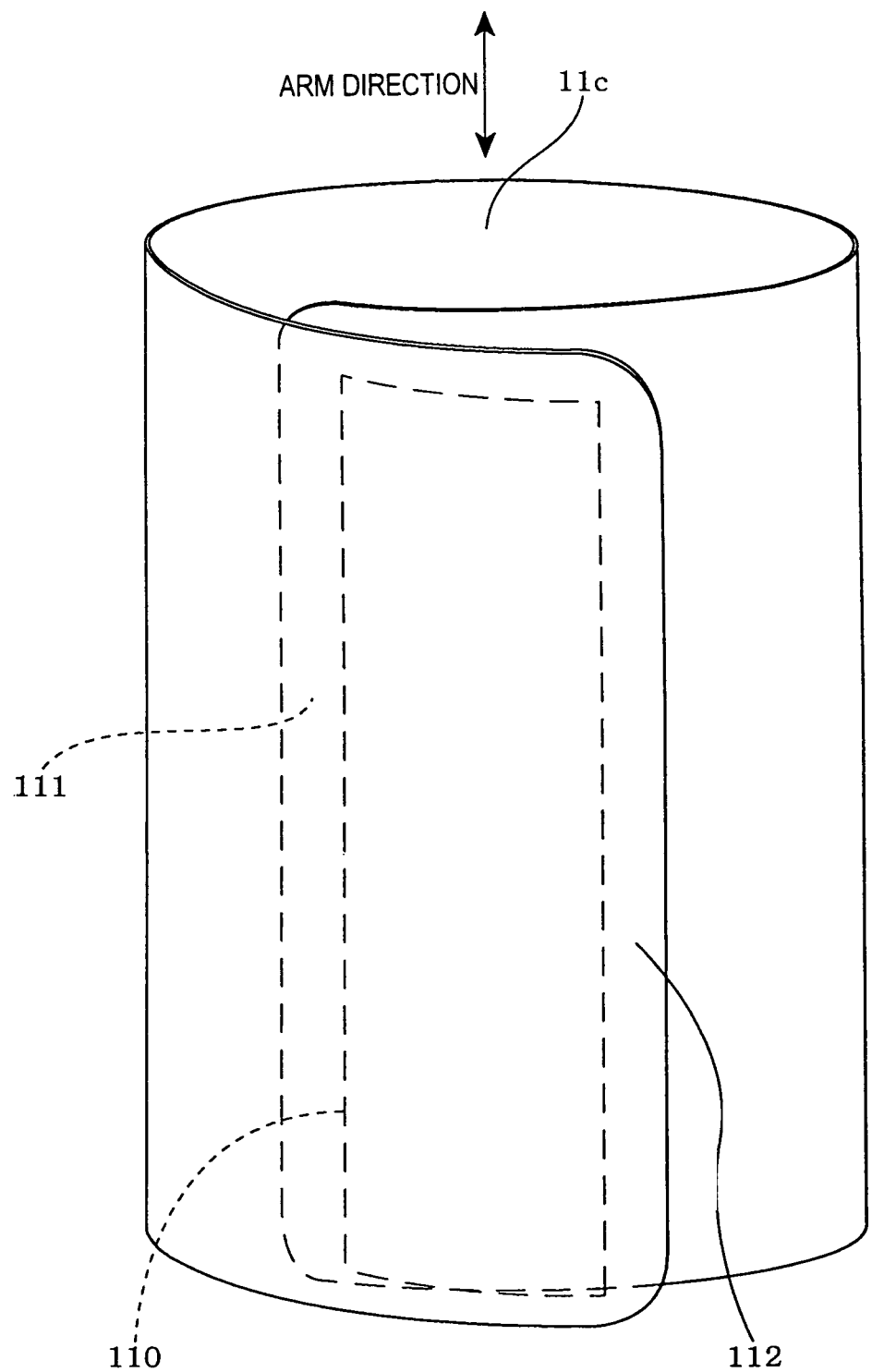
FIG. 12 shows a schematic perspective view for explaining a flexible cuff and a fabric elastic member, according to a second embodiment of a cuff for blood pressure meter of the present invention.

FIG. 12 shows a schematic perspective view for explaining the flexible cuff and the fabric elastic member, according to the second embodiment of the cuff for blood pressure meter of the present invention.

Figure 13:
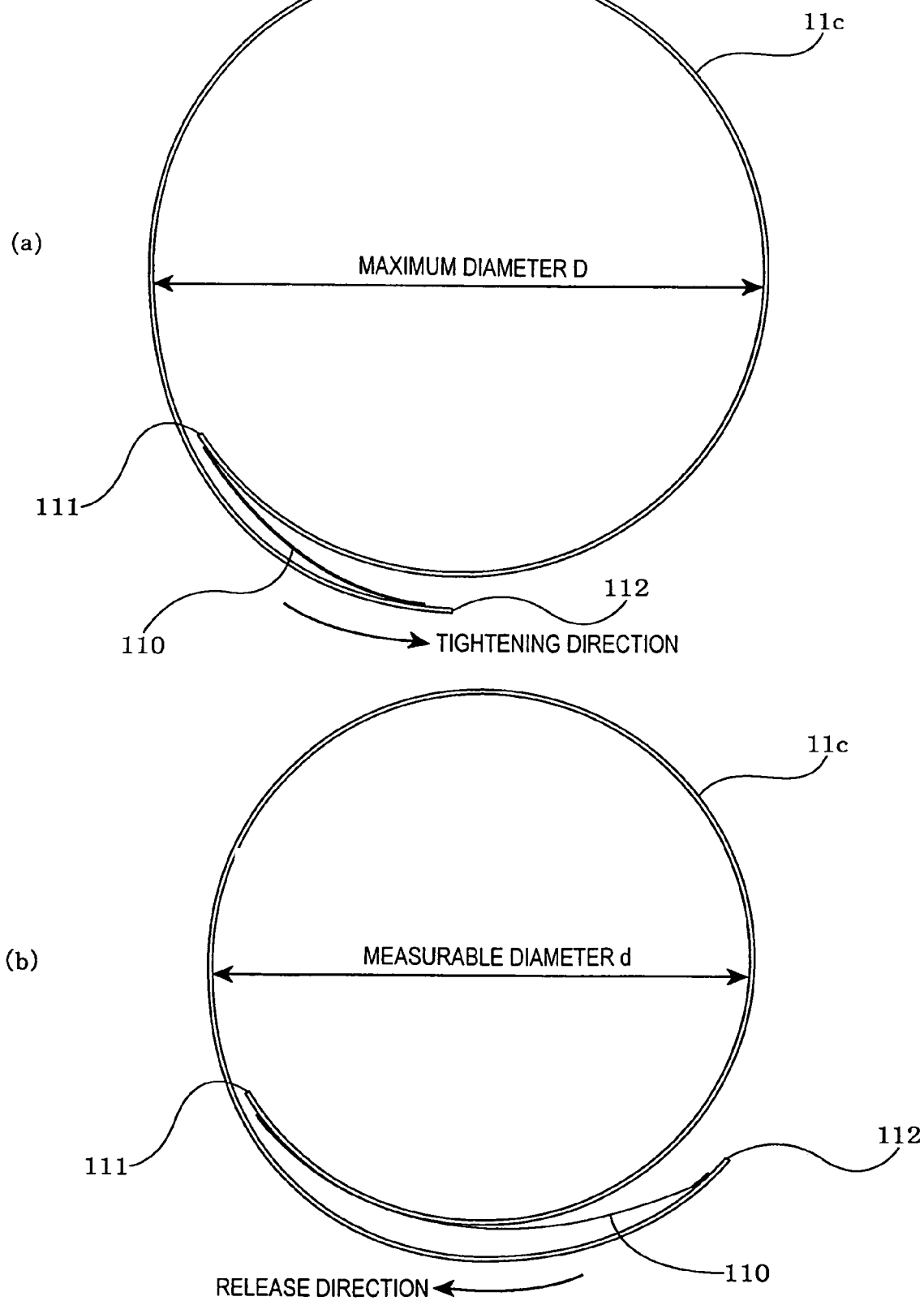
FIG. 13 are top views of FIG. 12, wherein (a) shows a schematic diagram in the state of a maximum diameter D, and (b) shows a schematic diagram in the state of a measurable diameter d.

Furthermore, FIG. 13 are top views of FIG. 12, wherein (a) shows a schematic diagram in the state of a maximum diameter D, and (b) shows a schematic diagram in the state of a measurable diameter d. In addition, FIG. 13 show a gap provided between an inner end 111 and an outer end 112 so that the structure of a fabric elastic member 110 can be easily understood.

In FIGS. 12 and 13, the flexible cuff 11c (generally referred to as a cuff) is made of a flexible resin sheet, and is curved and formed into a cylindrical shape with a diameter equal to or more than the maximum diameter D so that the outer end 112 is stacked on the inner end 111 so as to be wound around the inner end 111. Moreover, in the flexible cuff 11c, the inner end 111 and the outer end 112 are coupled together by the fabric elastic member 110. In addition, the maximum diameter D is a diameter at which an arm (not shown) is inserted into the flexible cuff 11c.

Furthermore, the flexible cuff 11c in the present embodiment is reduced in thickness to improve adaptability to the shape of the arm, so that the resilience of the shape of the flexible cuff 11c is small.

Moreover, the cylindrical air bag 12 is affixed to the inside of the flexible cuff 11c. The pipe 121 is projectingly provided in the air bag 12 in the arm direction, and air is put in via the pipe 121 when a blood pressure is measured.

<Fabric Elastic Member>

The fabric elastic member 110 is made of woven fabric (e.g., 2-way cloth), and formed into a substantially rectangular shape longer in the arm direction. The fabric elastic member 110 is foldable and extends in all directions, and is restored to its original shape from the extended state. One end of this fabric elastic member 110 is attached to the front surface of the inner end 111 of the flexible cuff 11c by, for example, stitching, adhesive bonding or welding. The other end is also attached to the rear surface of the outer end 112 of the flexible cuff 11c by, for example, stitching, adhesive bonding or welding.

In addition, the position to attach the fabric elastic member 110 is not limited to the above-mentioned position, and, for example, the respective ends of the fabric elastic member 110 may be attached to the edge on the side of the inner end 111 and the edge on the side of the outer end 112.

When the fabric elastic member 110 is restored to its original shape from the extended state, the flexible cuff 11c is in a cylindrical shape with the maximum diameter D, as shown in FIG. 13(a). That is, when a holding mechanism 3 untightens the flexible cuff 11c, the flexible cuff 11c is automatically expanded to the maximum diameter D by the resilience of the fabric elastic member 110, and held in the cylindrical shape by slight rigidity (shape retaining force) of the flexible cuff 11c. Therefore, the user can easily insert the arm into the flexible cuff 11c.

Moreover, when the fabric elastic member 110 is tightened by a tightening mechanism 2 with the arm inserted, the fabric elastic member 110 extends in the circumferential direction as shown in FIG. 13(b), so that the flexible cuff 11c is in a cylindrical shape with the measurable diameter d (d<D). In addition, the fabric elastic member 110 can extend until the flexible cuff 11c is in a cylindrical shape with a measurable minimum diameter d' (not shown).

Here, since the fabric elastic member 110 can extend in all directions, the fabric elastic member 110 flexibly deforms, and it is possible to avoid the problem of an impaired fitted feeling. That is, the flexible cuff 11c is structured to be extendable so that the diameter of the upper side of the flexible cuff 11c is smaller than the diameter of the lower side in accordance with the arm gradually becoming thinner from the elbow without disturbing the flexibility of the flexible cuff 11c, thereby enabling the improvement of the fittability of the flexible cuff 11c. Moreover, it is impossible to adapt to various shapes of arms. Therefore, even in the case of, for example, a muscular arm, the arm is uniformly compressed by the airbag 12, and the blood pressure can be accurately measured.

Furthermore, the fabric elastic member 110 has a length (width) substantially equal to the width of the flexible cuff 11c in the arm direction. Thus, the flexible cuff 11c and the fabric elastic member 110 become a substantially cylindrical annular member, which can simplify the shape and improves the adaptability of the flexible cuff 11c to the shape of the arm. Moreover, the tightening force of the tightening mechanism 2 can also act on the upper and lower ends of the flexible cuff 11c, which can further improve the fittability.

In addition, one sheet of fabric elastic member 110 is used in the present embodiment, but the present invention is not limited to this. For example, although not shown, a plurality of band or string elastic members (e.g., rubber strings covered with a material having low contact resistance) can be used instead of the fabric elastic member 110. Moreover, these band or string elastic members are typically used in parallel or in a crossed state (e.g., a tucked state). Further, the resilience, maximum extension rate or the like of the elastic members disposed in the upper and lower parts of the flexible cuff 11c can be adjusted to further improve the fittability to the arm.

The use and operation of the cuff for blood pressure meter having the above-mentioned configuration are described.

First, in the cuff for blood pressure meter of the present embodiment, the flexible cuff 11c is kept expanded to the maximum diameter D by the resilience of the fabric elastic member 110, by the rigidity of the flexible cuff 11c and by the tightening mechanism 2. Thus, the user of the cuff for blood pressure meter who is to have the blood pressure measured can easily insert one of the arms used for the measurement into the sufficiently expanded flexible cuff 11c.

Then, the user rotates a knob 21 to tighten the flexible cuff 11c from the entire circumferential direction. At this point, the fabric elastic member 110 freely extends in accordance with the flexible cuff 11c, so that the flexible cuff 11c can tighten the arm while deforming into a shape corresponding to the shape of the arm, thereby enabling the improvement of the fittability to the arm.

Then, air is put into the air bag 12, and the blood pressure is measured. When the air is put into the air bag 12, the flexible cuff 11c appropriately deforms, so that it is possible to prevent a problem of strongly compressing a particular part.

Then, the measurement of the blood pressure is displayed, and when the air is removed from the air bag 12, the user presses down a release lever 36 to cancel the holding state. At this point, when the holding state is cancelled, the flexible cuff 11c is automatically expanded without fail by the resilience of the fabric elastic member 110, and expanded to the maximum diameter D. Then, the flexible cuff 11c is maintained so that the arm can be easily inserted therein and removed therefrom.

Then, the user removes the left arm from the air bag 12, returns the cuff for blood pressure meter, and finishes the blood pressure measurement.

As described above, according to the cuff for blood pressure meter of the present embodiment, the arm can be easily and rapidly removed from the flexible cuff 11c after the blood pressure measurement. Moreover, the arm can be easily inserted when the holding mechanism 3 is released, which does not bother the user and can improve operability. That is, it is possible to improve both the fittability and operability which have not been attained by conventional techniques. Moreover, owing to the improvement of the fittability, the arm is uniformly compressed by the air bag 12, and the blood pressure can be accurately measured.

Third Embodiment

A third embodiment of a cuff for blood pressure meter of the present invention will hereinafter be described with reference to the drawings.

Figure 14:
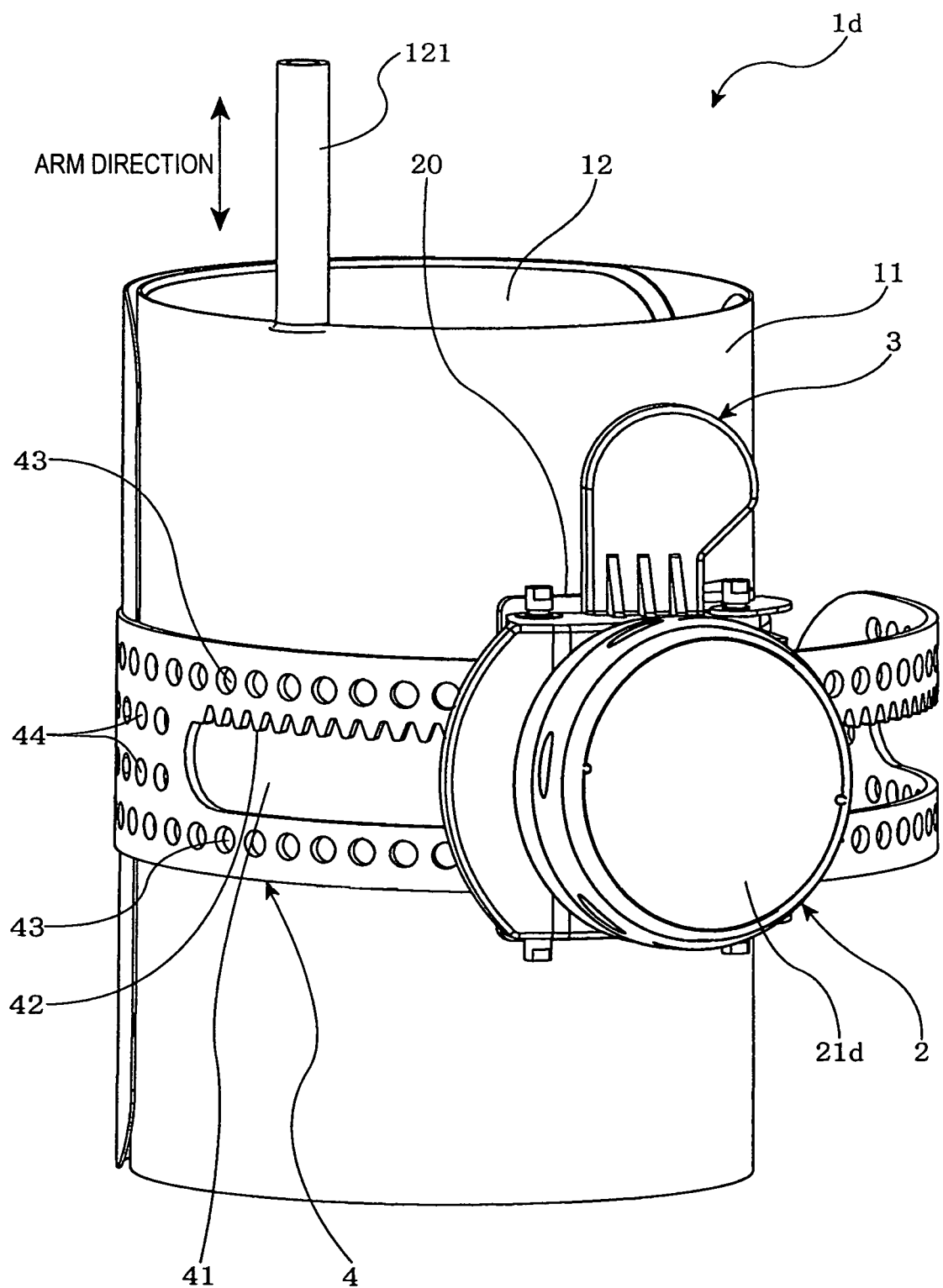
FIG. 14 shows a schematic perspective view in which a protective cover has been removed, according to a third embodiment of a cuff for blood pressure meter of the present invention.

FIG. 14 shows a schematic perspective view in which a protective cover has been removed, according to the third embodiment of the cuff for blood pressure meter of the present invention.

In FIG. 14, a cuff for blood pressure meter 1d is different from the cuff for blood pressure meter 1 in the first embodiment in that a knob 21 comprises noiseproof means. The cuff for blood pressure meter 1d is also different in that it comprises an interference member 281 which reduces impact noise produced when a release lever 36 is closed. It is to be noted that the configuration is substantially similar to that in the first embodiment in other respects.

Figure 15:
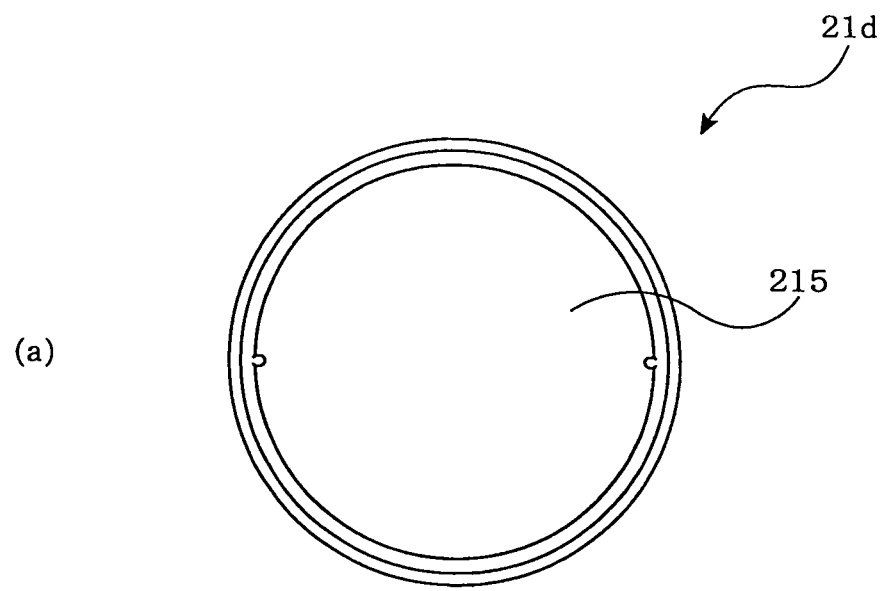
FIG. 15 are schematic diagrams for explaining the external structure of a knob, according to the third embodiment of the cuff for blood pressure meter of the present invention, wherein (a) shows a plan view, (b) shows a side view, and (c) shows a rear view.
Figure 15:
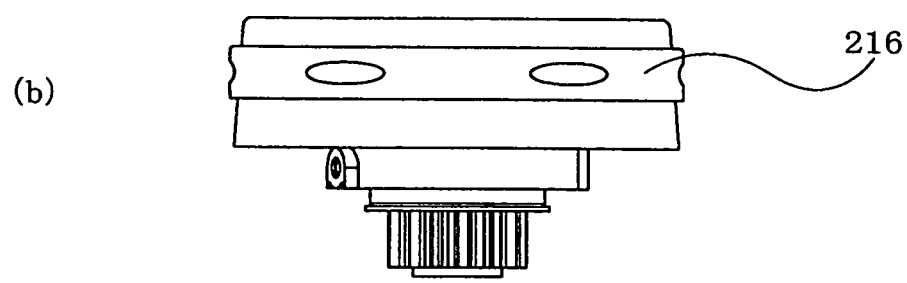
Figure 15:
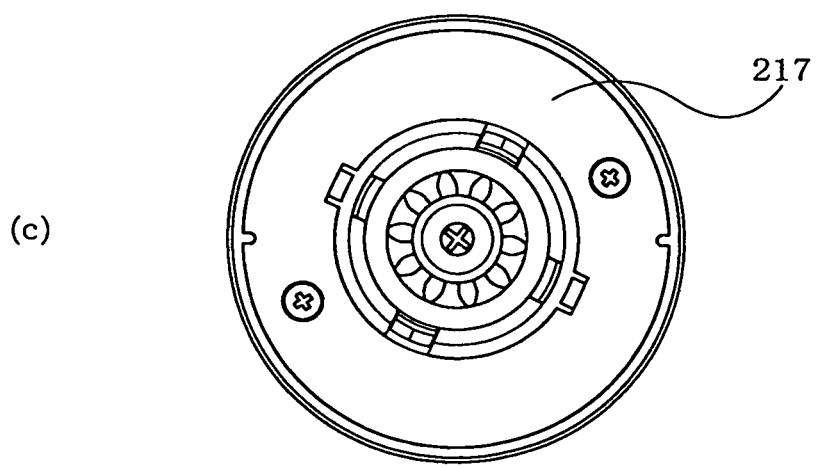

FIG. 15 are schematic diagrams for explaining the external structure of a knob, according to the third embodiment of the cuff for blood pressure meter of the present invention, wherein (a) shows a plan view, (b) shows a side view, and (c) shows a rear view.

In FIG. 15, a noise insulating member is attached to the knob 21d as the noiseproof means. The noise insulating member in the present embodiment includes a front cover 215, a side rubber 216 and a rear cover 217.

The front cover 215 is a circular plate made of, for example, a metal. This front cover 215 is attached to the upper surface of the knob 21d by, for example, an adhesive or a double-sided tape.

The side rubber 216 is a rubber belt. A plurality of concave portions are formed in the side rubber 216, and function as a slip resistance. This side rubber 216 is attached to the side surface of the knob 21d.

The rear cover 217 is an annular plate made of, for example, a metal. This rear cover 217 is attached to the top of the knob 21d by, for example, screws. Moreover, for example, a noise insulating sheet (not shown) may be affixed to the rear cover 217.

Figure 16:
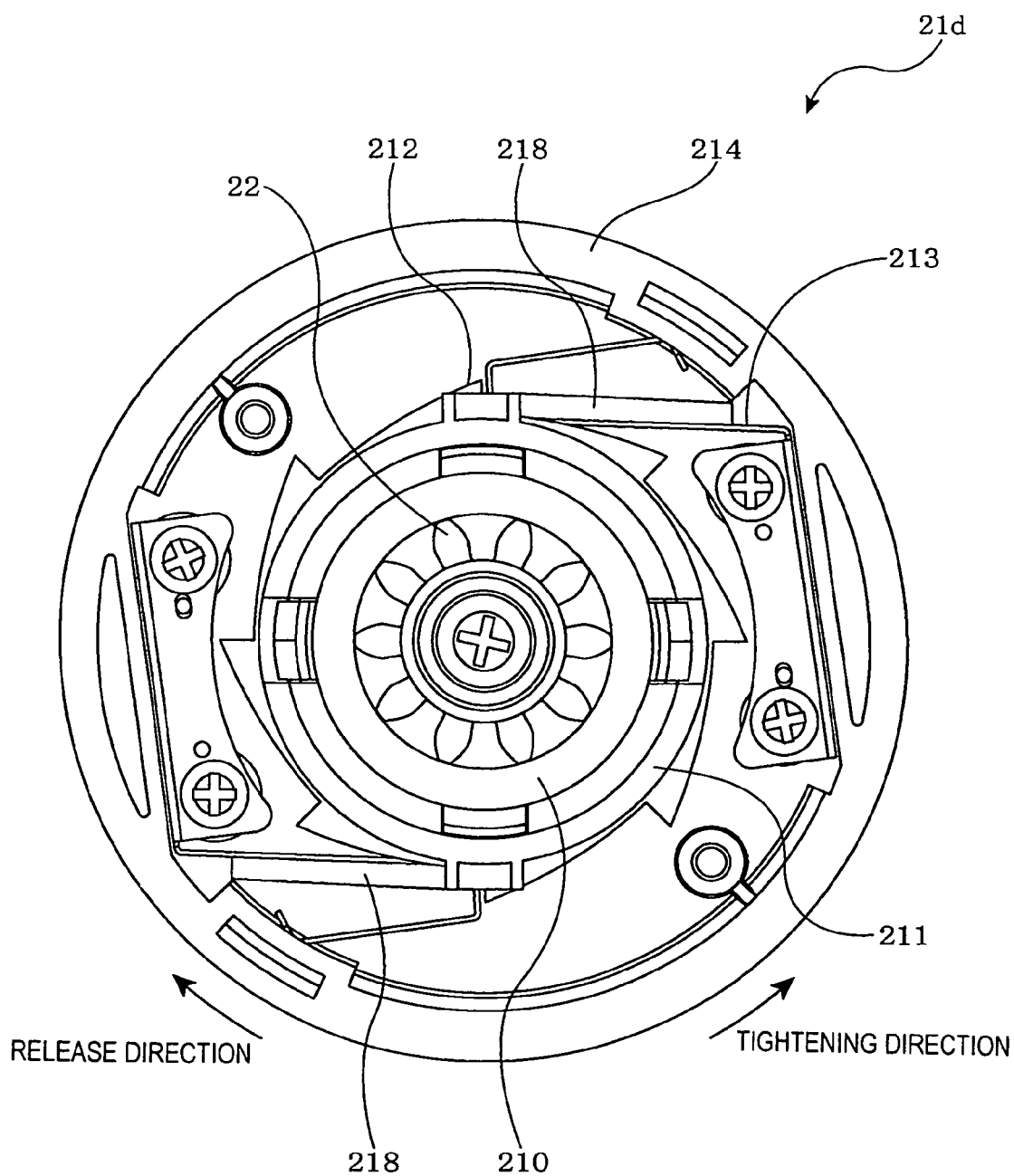
FIG. 16 shows a schematic enlarged rear view for explaining the internal structure of the knob, according to the third embodiment of the cuff for blood pressure meter of the present invention.

FIG. 16 shows a schematic enlarged rear view for explaining the internal structure of the knob, according to the third embodiment of the cuff for blood pressure meter of the present invention.

In FIG. 16, a noiseproof sheet 218 is attached to a leaf spring 213 which is a noise source, in the knob 21d.

The noiseproof sheet 218 is a band member made of a visco-elastic polymeric compound, urethane or the like.

This makes it possible to effectively reduce noise produced when a ratchet mechanism and a torque limiter mechanism operate. That is, the noiseproof sheet 218 attached to the leaf spring 213 reduces the noise itself, and the front cover 215, the side rubber 216 and the rear cover 217 prevent the produced noise from easily transmitted to the outside of the knob 21d. It is also possible to simplify the structure, and reduce manufacturing costs.

Moreover, the noiseproof sheet 218 has the effect of reducing the frequency of the noise. Thus, high-frequency noise is changed to low-frequency noise, so that offensive noise can be effectively inhibited.

Figure 17:
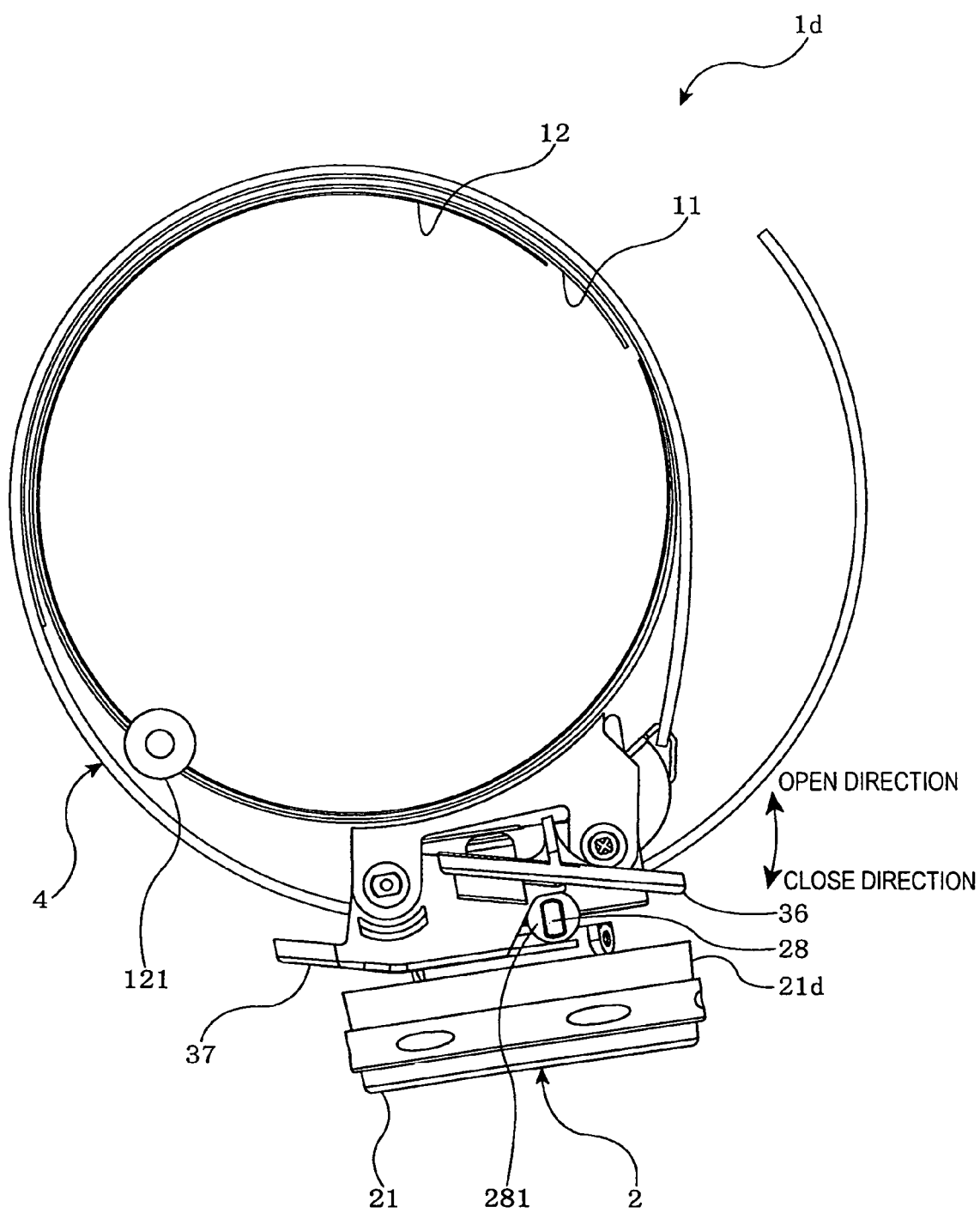
FIG. 17 shows a schematic top view of FIG. 14.

FIG. 17 shows a schematic top view of FIG. 14.

Figure 18:
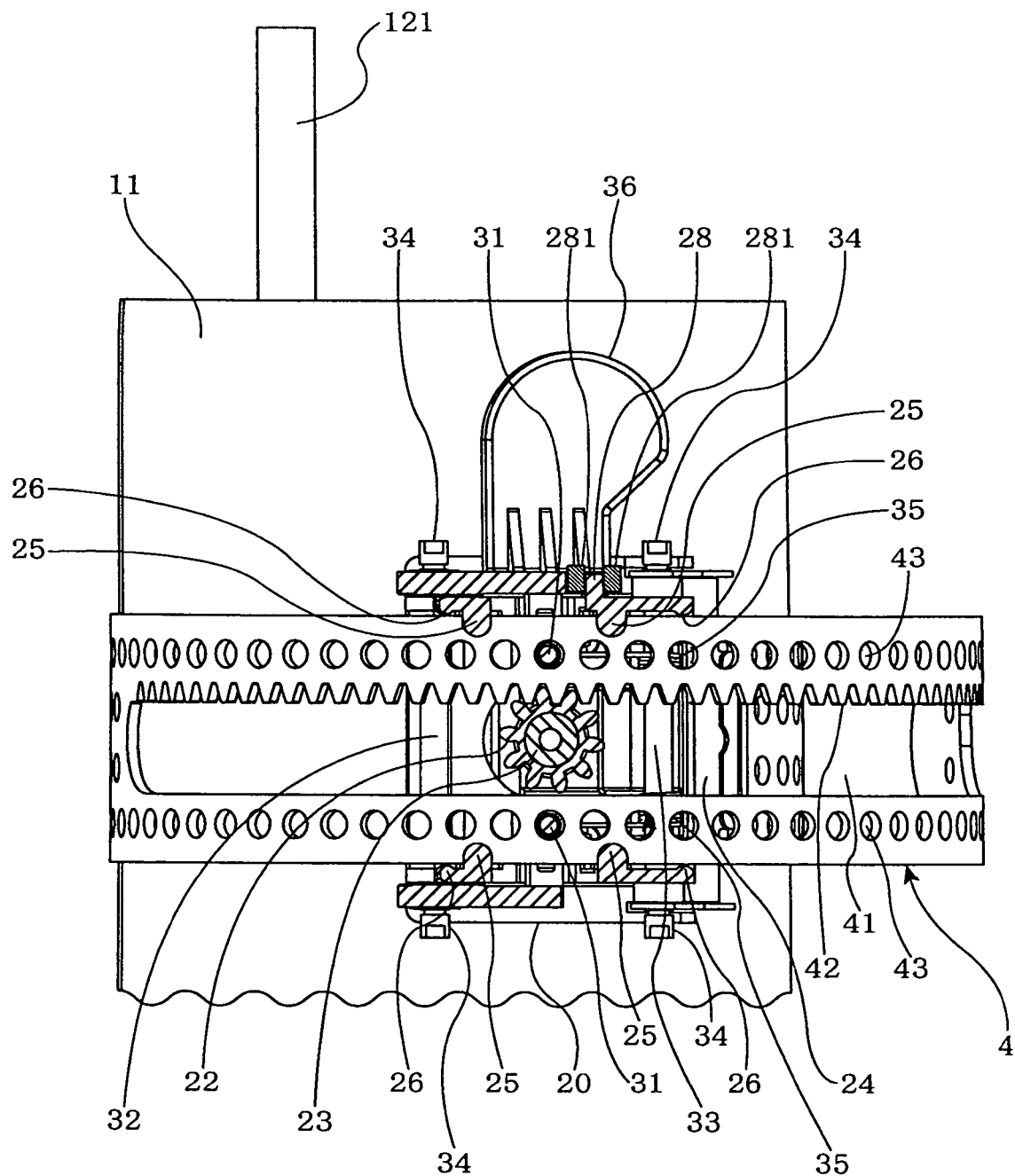
FIG. 18 shows a schematic sectional view in a front surface direction for explaining a tightening mechanism and a holding mechanism, according to the third embodiment of the cuff for blood pressure meter of the present invention.

Further, FIG. 18 shows a schematic sectional view in a front surface direction for explaining a tightening mechanism and a holding mechanism, according to the third embodiment of the cuff for blood pressure meter of the present invention.

In FIGS. 17 and 18, in the cuff for blood pressure meter 1d, the interference member 281 is attached to the stopper 28.

This interference member 281 is a thick circular plate made of rubber, urethane or the like. A substantially rectangular through-hole is formed in the center of this circular plate. The stopper 28 is inserted into this through-hole so that the interference member 281 is attached to the stopper 28.

When the tightening belt 4 moves in the tightening direction, holding pins 31 repeat the operation of coming out of holding holes 43 and the operation of being inserted into the holding holes 43. Further, when the holding pins 31 are inserted into the holding holes 43, the coupling portion 37 coupled to the release lever 36 contacts the side surface of the interference member 281. That is, due to the spring force of a spring 35, the coupling portion 37 collides with the interference member 281 and stops. At this point, since the coupling portion 37 collides with the interference member 281, impact noise can be significantly reduced.

In addition, the coupling portion 37 directly bumps into the stopper 28 due to the spring force of the spring 35 in the first embodiment. On the contrary, the provision of the interference member 281 enables a significant reduction of the impact noise.

As described above, the cuff for blood pressure meter 1d of the present embodiment is capable of effectively reducing the noise produced during operation. It is also possible to simplify the structure, and reduce manufacturing costs.

While the preferred embodiments have been shown and described in connection with the cuff for blood pressure meter of the present invention, the cuff for blood pressure meter according to the present invention is not exclusively limited to the embodiments described above, and various modifications can be made within the scope of the present invention.

For example, the rack 42 and the holding holes 43 are formed in the tightening belt 4 in the configurations in the embodiments described above, but the present invention is not limited to this. Although not shown, for example, the rack 42 and the holding holes 43 may be formed in a thickly formed flexible cuff or in a belt which is formed integrally with the flexible cuff 11. Alternatively, the rack 42 and the holding holes 43 may be formed in the thickly formed flexible cuff or in the belt which is formed integrally with the flexible cuff 11, and the rack 42 and the holding holes 43 may also be formed in the tightening belt 4.

Furthermore, the user rotates the knob 21 by hand in the configurations in the embodiments described above, but the present invention is not limited to this. Although not shown, for example, the pinion gear 22 may be rotated using drive means such as a motor instead of the knob 21. This makes it possible to automate the tightening of the flexible cuff 11, and further improve usability.

Still further, the pinion gear 22 is used as rack feed means to convert the rotational movement of the pinion gear 22 into the linear movement of the rack 42 in the embodiments described above, but the rack feed means is not limited to the pinion gear 22. For example, a worm gear (or a simple worm) may be used instead of the pinion gear 22 to convert the rotational movement of the worm gear (or the simple worm) into the linear movement of the rack 42.

The invention claimed is:

1. A cuff for blood pressure meter adapted to tighten a part of a living body, comprising:

a tightening member tightening a part of a living body and having a flexible core and a tightening belt which has an opening formed in a longitudinal direction thereof wounding around an outer periphery of the flexible core;

a tightening mechanism equipped with a rack formed integrally with the tightening belt at the opening formed on the tightening belt, the rack is provided on a longitudinal side of the tightening belt, rack feed means for gearing with the rack, and a knob rotating the rack feed means; and a holding mechanism equipped with a plurality of holding holes formed on the tightening belt and facing to each other across the opening of the tightening belt and holding members which are a pair of holding pins rotatably supported with a shaft and which engage with the plurality of holding holes, wherein the holding mechanism has urging means for urging the pair of holding pins in a direction to engage into the plurality of holding holes so that when the knob is rotated in a tightening direction, the pair of holding pins comes out of two holding holes among the plurality of holding holes against an urging force of the urging means, when the knob is further rotated in the tightening direction, the tightening belt moves in the tightening direction, and when another two holding holes among the plurality of holding holes located on a release direction side of the plurality of holding holes move to positions of the pair of holding pins, the pair of holding pins engages with the another two holding holes by the urging force.

2. The cuff for blood pressure meter according to claim 1, wherein one end of the flexible core is wound into other end, and the one end and the other end of the flexible core are coupled together by at least one of fabric, band and string elastic members which urges the flexible core in a release direction.

3. The cuff for blood pressure meter according to claim 2, wherein the elastic member has about the same width as the flexible core.

4. The cuff for blood pressure meter according to claim 2, wherein the tightening belt holds a condition where one end of the flexible core is wound into the other end.

5. The cuff for blood pressure meter according to claim 1, wherein the tightening belt has a width equal to or more than 20% and equal to or less than 80% of a width of the flexible core, and the tightening belt is put in the center of the flexible core.

6. The cuff for blood pressure meter according to claim 1, wherein a tooth thickness of the rack is equal to a thickness of the tightening member belt.

7. The cuff for blood pressure meter according to claim 1, wherein the rack feed means is a pinion gear, a worm gear or a worm.

8. The cuff for blood pressure meter according to claim 1, wherein the knob has a ratchet mechanism which rotates the rack feed means in the tightening direction, and a torque limiter mechanism.

9. The cuff for blood pressure meter according to claim 8, wherein the knob includes noiseproof means.

10. The cuff for blood pressure meter according to claim 9, wherein the noiseproof means is a noise insulating member attached to the knob and/or a noiseproof sheet attached to a noise source in the knob.

11. The cuff for blood pressure meter according to claim 1, wherein the holding mechanism has a release lever to force the pair of holding pins out of the holding holes.

12. The cuff for blood pressure meter according to claim 11, further comprising an interference member which reduces impact noise produced when the release lever is closed.

13. The cuff for blood pressure meter according to claim 1, wherein the racks are formed opposite to each other on both ends of a longitudinal direction of the tightening belt.

14. The cuff for blood pressure meter according to claim 1, wherein the rack is a double rack.

15. The cuff for blood pressure meter according to claim 1, wherein the knob is immovably fixed to the holding mechanism.

16. The cuff for blood pressure meter according to claim 2, wherein the one end and the other end of the flexible core are not fixed each other.

17. The cuff for blood pressure meter according to claim 1, wherein the tightening belt includes an elongated opening having the rack extending along one side of the opening, and the plurality of holding holes arranged to sandwich the opening, and the holding mechanism includes a spring, as the urging means, to push the pair of holding pins into the holding holes, and a release lever engaging the pair of holding pins so that when the release lever is pushed, the pair of holding pins is pushed to disengage from the holding holes.

* * * * *